(12) United States Patent
English et al.

(10) Patent No.: US 8,735,560 B1
(45) Date of Patent: May 27, 2014

(54) MULTIPLE DOMAIN LEPIDOPTERAN ACTIVE TOXIN PROTEINS

(75) Inventors: Leigh H. English, St. Louis, MO (US); Deborah G. Rucker, St. Louis, MO (US); Victor M. Guzov, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 262 days.

(21) Appl. No.: 13/038,720

(22) Filed: Mar. 2, 2011

Related U.S. Application Data

(60) Provisional application No. 61/309,738, filed on Mar. 2, 2010.

(51) Int. Cl.
*C07H 21/04* (2006.01)
*A01H 5/00* (2006.01)
*C12N 5/14* (2006.01)
*C12N 15/82* (2006.01)
*C12N 15/74* (2006.01)

(52) U.S. Cl.
USPC ........ 536/23.71; 800/302; 435/419; 435/468; 435/471

(58) Field of Classification Search
None
See application file for complete search history.

(56) References Cited

U.S. PATENT DOCUMENTS

| | | | |
|---|---|---|---|
| 5,736,131 A * | 4/1998 | Bosch et al. | 800/300 |
| 5,880,275 A | 3/1999 | Fischhoff et al. | |
| 6,033,874 A | 3/2000 | Baum et al. | |
| 6,501,009 B1 | 12/2002 | Romano | |
| 7,030,295 B2 | 4/2006 | Chen et al. | |
| 7,064,249 B2 | 6/2006 | Corbin et al. | |
| 7,070,982 B2 | 7/2006 | Malvar et al. | |
| 7,927,598 B2 | 4/2011 | Malvar et al. | |
| 8,034,997 B2 | 10/2011 | Bogdanova et al. | |
| 2006/0014936 A1 * | 1/2006 | Malvar et al. | 530/387.1 |
| 2006/0021087 A1 | 1/2006 | Baum et al. | |
| 2006/0112447 A1 | 5/2006 | Bogdanova et al. | |
| 2010/0017914 A1 * | 1/2010 | Hart et al. | 800/279 |

FOREIGN PATENT DOCUMENTS

WO    2005/110068    11/2005

OTHER PUBLICATIONS

Pardo-Lopez et al, Peptides 30:589-95 (2009).*
Avisar et al., Phtoparasitica 30(2)210-11 (2002).*
Xia et al., Chin Sci Bull 53(20):3178-84 (2008).*

* cited by examiner

*Primary Examiner* — Medina A Ibrahim
*Assistant Examiner* — Russell Boggs
(74) *Attorney, Agent, or Firm* — Thompson Coburn LLP; J. Wendy Davis

(57) ABSTRACT

Novel synthetic *Bacillus thuringiensis* crystal proteins exhibiting insect inhibitory activity is disclosed. Polynucleotides encoding the crystal protein, transgenic plants and microorganisms that contain the polynucleotides, isolated peptides derived from the crystal protein, and antibodies directed against the crystal protein are also provided. Methods of using the crystal protein and polynucleotides encoding the crystal protein to control Lepidopteran insects are also disclosed.

23 Claims, No Drawings

MULTIPLE DOMAIN LEPIDOPTERAN ACTIVE TOXIN PROTEINS

CROSS-REFERENCE TO RELATED APPLICATIONS

This application is a non-provisional U.S. patent application which claims benefit under 35 U.S.C. §119(e) of U.S. Provisional Patent Application Ser. No. 61/309,738, filed Mar. 2, 2010, and incorporated herein by reference in its entirety.

INCORPORATION OF SEQUENCE LISTING

A computer readable form of the sequence listing is provided herewith, containing the file named "38_21(54885) B_SEQ_LST", which is 100776 bytes in size (measured in MS-DOS), and is herein incorporated by reference. This Sequence Listing consists of SEQ ID NOs:1-13.

FIELD OF THE INVENTION

This invention relates generally to the field of insect inhibitory *Bacillus thuringiensis* proteins and, more particularly, to *B. thuringiensis* crystal proteins that inhibit Lepidopteran insects. Isolated polynucleotides and proteins, transgenic plants and related methods that provide for inhibition of Lepidopteran insects are described. Also described are methods for combining the *B. thuringiensis* crystal proteins that inhibit Lepidopteran insects with distinct insect control agents to obtain increased levels of Lepidopteran insect inhibition, Lepidopteran insect resistance management, or an expanded spectrum of insect pest control.

BACKGROUND OF THE INVENTION

Insecticidal protein derived from *Bacillus thuringiensis* bacterial species (i.e., Bt proteins) are known in the art. A small number of the Bt proteins have been used for commercial purposes. Recent detection of Bt-resistant pests targeted for control by certain commercial products expressing Bt proteins has heightened the necessity for the discovery of novel Bt proteins that are capable of controlling such resistant species, preferably by modes of action that are different when compared to that exhibited by the protein to which the pests have become resistant. Therefore, it is important to identify Bt proteins that are effective in controlling such targeted pests, particularly the targeted pests that have developed resistance to certain commercial Bt proteins.

SUMMARY OF THE INVENTION

The present invention provides a polynucleotide which encodes an insect inhibitory protein comprising a Cry1 polypeptide, wherein said Cry1 polypeptide comprises a first domain III, and a supplemental Cry protein domain III polypeptide sequence operably linked to said Cry1 polypeptide, and wherein said operable linkage of said supplemental domain III is (a) to the N-terminus of said first domain III polypeptide sequence; or (b) to the C-terminus of said first domain III polypeptide sequence; and
said Cry1 polypeptide is selected from the group consisting of a Cry1A, a Cry1B, a Cry1C, a Cry1D, a Cry1E, a Cry1F, a Cry1H, a Cry1I, a Cry1J, a Cry1K, Cry1L, and a Cry1 chimeric polypeptide produced from two or more different Cry1 proteins; or said Cry1 polypeptide is a Cry1A polypeptide selected from the group consisting of a Cry1Aa, a Cry1Ab, a Cry1Ac, a Cry1Ad, a Cry1Ae, a Cry1Af, a Cry1Ah, and Cry1Ai polypeptide; or said supplemental domain III polypeptide sequence comprises an amino acid sequence of a native Cry protein domain III polypeptide sequence; or said supplemental Cry protein domain III polypeptide sequence comprises an engineered domain III polypeptide sequence comprising, optionally, (a) amino acid substitutions, insertions, and/or deletions compared to an amino acid sequence of a native Cry protein domain III polypeptide sequence, or (b) segments of two or more Cry protein domain III amino acid sequences, or (c) amino acid substitutions, insertions, and/or deletions in one or more segments of said engineered domain III polypeptide sequence of optional subpart (b); or wherein said Cry1 polypeptide comprises a Cry1A polypeptide and wherein said supplemental Cry protein domain III polypeptide sequence is selected from the group consisting of a Cry1B, a Cry1C, a Cry1D, a Cry1E, a Cry1F, a Cry1H, a Cry1I, a Cry1J, a Cry1K, a Cry1L, a Cry2A, a Cry3A, a Cry 3B, a Cry9A domain III polypeptide sequence, and an engineered variant thereof; or wherein said Cry1A polypeptide comprises a Cry1Ac polypeptide and wherein said supplemental Cry protein domain III polypeptide sequence is selected from the group consisting of a Cry1F, a Cry2Ab, a Cry 3Bb, a Cry9A domain III polypeptide sequence, and an engineered variant thereof; or wherein said supplemental Cry protein domain III polypeptide sequence is a Cry1F domain III polypeptide sequence and wherein said insect inhibitory protein comprises a polypeptide sequence that is at least 90% identical to SEQ ID NO:1; or wherein said insect inhibitory protein exhibits improved insecticidal activity against *Agrotis, Helicoverpa,* or *Striacosta* relative to a Cry1Ac polypeptide; or wherein said supplemental Cry protein domain III polypeptide sequence is a Cry2Ab domain III polypeptide sequence and wherein said insect inhibitory protein comprises a polypeptide sequence that is at least 90% identical to SEQ ID NO:3; or wherein said insect inhibitory protein exhibits improved insecticidal activity against *Helicoverpa* or *Striacosta* relative to a Cry1 Ac polypeptide; or wherein said supplemental Cry protein domain III polypeptide sequence is a Cry3Bb domain III polypeptide sequence and wherein said insect inhibitory protein comprises a polypeptide sequence that is at least 90% identical to SEQ ID NO:5; or wherein said insect inhibitory protein exhibits improved insecticidal activity against *Striacosta* relative to a Cry1Ac polypeptide; or a transgenic plant or plant part derived therefrom comprising a polynucleotide of any one of the foregoing; or wherein said plant or plant part comprises a concentration of said insect inhibitory protein encoded by said polynucleotide that inhibits a Lepidopteran insect; or wherein said Lepidopteran insect is *Agrotis, Helicoverpa, Ostrinia, Striacosta,* or *Spodoptera*; or wherein said plant part is selected from a leaf, a stem, a flower, a sepal, a fruit, a root, or a seed; or a transformed host cell comprising a polynucleotide of any one of the foregoing; or wherein said host cell is a bacterial cell or a plant cell; or wherein said plant cell is selected from the group consisting of alfalfa, banana, barley, broccoli, bean, broccoli, cabbage, canola, carrot, cassava, castor, cauliflower, celery, chickpea, citrus, coconut, coffee, corn, clover, cotton, a cucurbit, Douglas fir, eggplant, eucalyptus, flax, garlic, grape, hops, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rye, safflower, shrub, sorghum, Southern pine, soybean, spinach, squash, strawberry, sugar beet, sugarcane, sunflower, sweet gum, sweet potato, switchgrass, tea, tobacco, tomato, triticale, turf grass, watermelon, and wheat plant cells; or wherein said plant cell is a corn plant cell; or a plant derived from said transformed plant host cell of any of the foregoing wherein said plant comprises said polynucleotide; or wherein said bacterial cell is selected from the group consisting of an *Agrobacterium*, a *Bacillus*, an *Escherichia*, a *Salmonella*, a *Pseudomonas*, and a *Rhizobium* bacterial cell; or wherein said bacterial cell is a *Bacillus thuringiensis* cell.

The present invention also provides a method for controlling a Lepidopteran insect comprising the steps of:

(a) providing a Lepidopteran insect inhibitory amount of an insect inhibitory protein, wherein said insect inhibitory protein is encoded by any one of the foregoing polynucleotides of this invention; and (b) contacting said Lepidopteran insect with said inhibitory amount of said insect inhibitory protein, thereby controlling a Lepidopteran insect; or wherein said Lepidopteran insect is *Agrotis, Spodoptera, Helicoverpa, Ostrinia,* or *Striacosta*; or wherein said Lepidopteran insect inhibitory amount of said polypeptide sequence is provided in a Lepidopteran insect diet in step (a) and said Lepidopteran insect is contacted in step (b) by permitting said Lepidopteran insect to feed on said diet; or wherein said Lepidopteran insect diet is a transgenic plant; or wherein said Lepidopteran insect inhibitory amount of said polypeptide sequence is provided in step (a) by spraying a composition comprising said polypeptide on a plant; or wherein said composition comprises bacterial cells or bacterial spores that express said polypeptide; or wherein said bacterial cells or bacterial spores are *Bacillus* cells or *Bacillus* spores; or wherein said composition comprises a parasporal crystal containing said polypeptide.

The present invention also provides an insect inhibitory protein comprising a Cry1 polypeptide wherein a supplemental Cry protein domain III polypeptide sequence is operably linked to the first domain III polypeptide sequence of said Cry1 polypeptide; or wherein said supplemental Cry protein domain III polypeptide sequence is operably linked to the N-terminus of said first domain III polypeptide sequence of said Cry1 polypeptide; or wherein said supplemental Cry protein domain III polypeptide sequence is operably linked to the C-terminus of said first domain III polypeptide sequence of said Cry1 polypeptide; or wherein said Cry1 polypeptide is selected from the group consisting of a Cry1A, a Cry1B, a Cry1C, a Cry1D, a Cry1E, a Cry1F, a Cry1H, a Cry1I, a Cry1J, a Cry1K, and a Cry1L polypeptide; or wherein said Cry1 polypeptide is a Cry1A polypeptide selected from the group consisting of a Cry1Aa, a Cry1Ab, a Cry1Ac, a Cry1Ad, a Cry1Ae, a Cry1Af, a Cry1Ah, and Cry1Ai polypeptide; or said supplemental domain III polypeptide sequence comprises an amino acid sequence of a native Cry protein domain III polypeptide sequence; or said supplemental Cry protein domain III polypeptide sequence comprises an engineered domain III polypeptide sequence comprising, optionally, (a) amino acid substitutions, insertions, and/or deletions compared to an amino acid sequence of a native Cry protein domain III polypeptide sequence, or (b) segments of two or more Cry protein domain III amino acid sequences, or (c) amino acid substitutions, insertions, and/or deletions in one or more segments of said engineered domain III polypeptide sequence of optional subpart (b); or wherein said Cry1 polypeptide comprises a Cry1A polypeptide and wherein said supplemental Cry protein domain III polypeptide sequence is selected from the group consisting of a Cry1B, a Cry1C, a Cry1D, a Cry1E, a Cry1F, a Cry1H, a Cry1I, a Cry1J, a Cry1K, a Cry1L, a Cry2A, a Cry3A, a Cry 3B, a Cry9A domain III polypeptide sequence, and an engineered variant thereof; or wherein said Cry1A polypeptide comprises a Cry1Ac polypeptide and wherein said supplemental Cry protein domain III polypeptide sequence is selected from the group consisting of a Cry1F, a Cry2Ab, a Cry 3Bb, a Cry9A domain III polypeptide sequence, and an engineered variant thereof; or wherein said supplemental Cry protein domain III polypeptide sequence is a Cry1F domain III polypeptide sequence and wherein said insect inhibitory protein comprises a polypeptide sequence that is at least 90% identical to SEQ ID NO:1; or wherein said insect inhibitory protein comprises a polypeptide sequence that is at least 95% identical to SEQ ID NO:1; or wherein said insect inhibitory protein comprises the polypeptide sequence of SEQ ID NO:1; or wherein said insect inhibitory protein exhibits improved insecticidal activity against *Agrotis, Helicoverpa,* or *Striacosta* relative to a Cry1 Ac polypeptide; or wherein said supplemental Cry protein domain III polypeptide sequence is a Cry2Ab domain III polypeptide sequence and wherein said insect inhibitory protein comprises a polypeptide sequence that is at least 90% identical to SEQ ID NO:3; or wherein said insect inhibitory protein comprises a polypeptide sequence that is at least 95% identical to SEQ ID NO:3; or wherein said insect inhibitory protein comprises the polypeptide sequence of SEQ ID NO:3; or wherein said insect inhibitory protein exhibits improved insecticidal activity against *Helicoverpa,* or *Striacosta* relative to a Cry1Ac polypeptide; or wherein said supplemental Cry protein domain III polypeptide sequence is a Cry3Bb domain III polypeptide sequence and wherein said insect inhibitory protein has a polypeptide sequence that is at least 90% identical to SEQ ID NO:5; or wherein said insect inhibitory protein comprises a polypeptide sequence that is at least 95% identical to SEQ ID NO:5; or wherein said insect inhibitory protein comprises the polypeptide sequence of SEQ ID NO:5; or wherein said insect inhibitory protein exhibits improved insecticidal activity against *Striacosta* relative to a Cry1Ac polypeptide.

DETAILED DESCRIPTION

Bt toxin proteins (or "Cry proteins") of the Cry1-9 and other classes such as Cry10-11, Cry21, and the like, are classes of toxin proteins that are known to exhibit a three dimensional three domain tertiary structure, generally consisting of domains referred to as domains I, II, and III. It has been discovered that the insecticidal portions of these insecticidal Bt toxins can be coupled, fused, linked connected, or mated to a supplemental Cry protein domain III, the resulting protein fusion or chimera exhibiting improved insecticidal activity selected from the group consisting of improved or larger host range specificity, improved or greater insecticidal activity, and the like, when compared to the Bt toxin lacking the supplemental domain III. The supplemental Cry protein domain III to which the insecticidal portion of the particular insecticidal Bt toxin is fused can be any native Bt insecticidal protein domain III or optionally any engineered domain III. For example, a Cry1Aa1 toxin portion can be fused at its carboxyl terminal end to a supplemental Cry protein domain III duplicated from the Cry1Aa1 toxin portion domain III, or from any other toxin portion domain III that is different from a Cry1Aa1 domain III. Such novel insecticidal toxin protein chimeras surprisingly exhibit an increased range of insecticidal activity directed to specific plant pests as well as an increase in insecticidal activity when compared to the insecticidal toxin protein portion lacking the supplemental Cry protein domain III amino acid segment. The supplemental Cry protein domain III polypeptide sequence can also comprise an engineered domain III polypeptide sequence comprising, optionally, (a) amino acid substitutions, insertions, or deletions compared to an amino acid sequence of a native Cry protein domain III polypeptide sequence, or (b) segments of two or more Cry protein domain III amino acid sequences, or (c) amino acid substitutions, insertions, or deletions in one or more segments of said engineered domain III polypeptide sequence of optional subpart (b).

The embodiments disclosed in this application correspond to and are applicable to any particular first three domain Cry toxin portion in which a supplemental Cry protein domain III from that or any other three domain Cry toxin is operably linked to the first three domain Cry toxin. The linkage can be insertion of the supplemental Cry protein domain III between domains 2 and 3 of the first three domain Cry toxin, or the supplemental Cry protein domain III can be linked to the carboxy terminus of the first cry toxin domain III. The supplemental Cry protein domain III can be a domain III that is the same as the domain III of the first Cry toxin or can be any other domain III obtained or derived from a second Cry toxin that is different from the first. The supplemental Cry protein domain III can consist of the amino acid sequence of a domain III from a second Cry toxin that is a member of the same category and class of Cry toxin to which the first Cry toxin has been assigned, or can consist of a domain III from a second Cry toxin that is a member of a completely different category and class of Cry toxin than that to which the first Cry toxin has been assigned. Schnepf et al (MMBR 1998 (62)775-806) describes the features of each individual category and class of three domain Cry toxin proteins, particularly with reference to identifying the range of amino acid sequences in each three domain protein that correspond to domains I, II and III, relative to the conserved homology blocks present in each category and class of three domain toxin proteins. In this case, the breakpoint to be used for insertion of a supplemental Cry protein domain III is considered to be within the amino acid segment that is positioned between any domain II and domain III of any particular three domain Cry toxin, more specifically, within homology block three, and the breakpoint to be used for insertion of a supplemental Cry protein domain III is considered to be within the amino acid segment that is positioned within homology block five of any particular three domain Cry toxin protein, the carboxy terminus of such domain III being positioned within homology block five, except for Cry2 classes of proteins, and then the carboxy terminus of the domain III of the protein to which the supplemental Cry protein domain III is to be incorporated lies within the amino acid segment of such Cry2 from about amino acid 560 to about amino acid 582.

Several such novel insecticidal toxin proteins are described herein, including T1C465 (SEQ ID NO:1), T1C467 (SEQ ID NO:3), and T1C469 (SEQ ID NO:5).

Accession No. NRRL B-50283 is an *E. coli* K12 strain containing plasmid vector pMON126556 deposited on Apr. 21, 2009 with the Agricultural Research Culture Collection, International Depository Authority, Northern Regional Research laboratory (NRRL), at 1815 North University Street, Peoria, Ill., USA Zip 61064. The plasmid contains an open reading frame as set forth in SEQ ID NO:2 encoding the TIC465 amino acid sequence as set forth in SEQ ID NO:1.

Accession No. NRRL B-50284 is an *E. coli* K12 strain containing plasmid vector pMON126559 has been deposited on Apr. 21, 2009 with the Agricultural Research Culture Collection, International Depository Authority, Northern Regional Research laboratory (NRRL), at 1815 North University Street, Peoria, Ill., USA Zip 61064. The plasmid contains an open reading frame as set forth in SEQ ID NO:4 encoding the TIC467 amino acid sequence as set forth in SEQ ID NO:3.

Accession No. NRRL B-50285 is an *E. coli* K12 strain containing plasmid vector pMON126560 has been deposited on Apr. 21, 2009 with the Agricultural Research Culture Collection, International Depository Authority, Northern Regional Research laboratory (NRRL), at 1815 North University Street, Peoria, Ill., USA Zip 61064. The plasmid contains an open reading frame as set forth in SEQ ID NO:6 encoding the TIC469 amino acid sequence as set forth in SEQ ID NO:5.

Transgenic plants expressing multi-domain toxin proteins that inhibit specific insect pests are provided by this invention, i.e., with reference to multi-domain toxin proteins it is intended to include insecticidal portions of Bt toxin proteins that are coupled, fused, linked, connected, or mated to a supplemental protein segment derived from a domain III of that or any other Bt toxin protein exhibiting a three domain type structure. The coupling, fusing, linking, connecting, or mating of the supplemental segment is generally at or near the carboxyl terminal end of the insecticidal portion of the reference Bt toxin protein, or alternatively, the supplemental Cry protein domain III segment can be inserted between the reference Bt toxin protein domain II and the reference Bt toxin protein domain III, so long as there are tandem domain III segments at the carboxyterminal end of the segment consisting of the domain I and domain II of the reference Bt toxin protein. Transgenic plants expressing novel proteins of the present invention inhibit Lepidopteran insects including, but not limited to, *Ostrinia nubilalis* (European Corn Borer), *Helicoverpa zea* (Corn Earworm), *Agrotis ipsilon* (Black cutworm), *Spodoptera frugiperda* (Fall Armyworm), and *Striacosta albicosta* (Western Bean Cutworm). Transgenic plants that express a TIC465-type protein of SEQ ID NO:1, an insect inhibitory fragment thereof, or a biological equivalent thereof and that provide protection against Lepidopteran insects including, but not limited to, *Ostrinia nubilalis* (European Corn Borer), *Helicoverpa zea* (Corn Earworm), *Agrotis ipsilon* (Black cutworm), *Spodoptera frugiperda* (Fall Armyworm) and *Striacosta albicosta* (Western Bean Cutworm) are specifically provided.

The novel toxin protein compositions disclosed herein will find particular utility as insect inhibitory agents for topical and/or systemic application to field crops, grasses, fruits and vegetables, and ornamental plants. The compositions can be applied in the form of crystal spore mixtures of *Bacillus thuringiensis* bacteria, or in other formulation methods such as whole cell preparations, cell extracts, cell suspensions, cell homogenates, cell lysates, cell supernatants, cell filtrates, or cell pellets of a cell culture (preferably a bacterial cell culture such as a *Bacillus thuringiensis* culture) that expresses one or more of the proteins of the present invention or applied in the form of a water dispersible granule or powder which may comprise lysed or unlysed bacterial cells, spores, or crystals containing one or more of the novel crystal proteins disclosed herein. Alternatively, the insect inhibitory composition may consist of a wettable powder, spray, emulsion, colloid, aqueous or organic solution, dust, pellet, or collodial concentrate.

It is entirely possible that insects may develop resistance to certain insecticides. Most insect resistance management strategies using genetically modified crops expressing insect inhibitory agents rely on the use of refuge areas that are comprised of crop plants that lack the insect inhibitory gene. In theory, the refuge provides a region in which non-resistant insect populations harboring non-resistant genetic alleles are maintained, lowering the potential for resistance to develop within the insect population. However, the refuge strategy suffers from several short-comings. First, the growers must accept reduced yields on the acreage planted with the insect inhibitory gene. Second, it is not clear that refuges will effectively control dominant resistance alleles that can arise in the insect population.

An insect resistance management strategy can employ transgenic crops that express two distinct insect inhibitory agents that operate through different modes of action. In this case, any insects with resistance to either one of the insect inhibitory agents will be controlled by the other insect inhibitory agent, thus reducing the chances of resistance developing in the insect population.

Proteins of the present invention can be combined together to provide two modes of action or can be combined individually with different Bt proteins toxic to the same insect pests to which the proteins of the present invention exhibit inhibitory function, or together with chemical insecticides or with dsRNA components that are designed to suppress essential genes in one or more target pests. These combinations can be provided in planta or as topical applications such as seed treatments.

For control of Lepidopteran pests, combinations of insect inhibitory multi-domain toxin proteins with Lepidopteran-active proteins such as Cry1A proteins (U.S. Pat. No. 5,880,275). Cry1B (U.S. patent application Ser. No. 10/525,318), Cry1C (U.S. Pat. No. 6,033,874), Cry1F, VIP proteins and VIP protein chimeras constructed using portions of crystalline Bt proteins, Cry1A/F chimeras (U.S. Pat. Nos. 7,070,982; 6,962,705; and 6,713,063), and a Cry2Ab protein (U.S. Pat. No. 7,064,249) are specifically contemplated. For control of Coleopteran pests, combinations of insect inhibitory multi-domain toxin proteins with Coleopteran-active proteins such as Cry3Bb (U.S. Pat. No. 6,501,009) are specifically contemplated.

DNA sequences encoding insect inhibitory multi-domain toxin protein molecules and other insect inhibitory agents such as double stranded RNA molecules and/or non-multi-domain toxin proteins can be combined in a single plant either through direct transformation, by breeding, or a combination thereof.

It is further anticipated that the combination of insect inhibitory multi-domain toxin protein molecules and other insect inhibitory agents such as double stranded RNA molecules and/or non-multi-domain toxin proteins can result in unexpected synergistic insect inhibitory effects that are not observed with either the multi-domain toxin insect inhibitory protein alone, the insect inhibitory ribonucleotide alone, or the non-multi-domain toxin insect inhibitory protein alone. Synergistic effects include but are not limited to, (i) quantitative changes in $LC_{50}$, $EC_{50}$, $IC_{50}$, percent mortality, or percent stunting values and (ii) qualitative changes in the spectrum of insect inhibition (i.e., Lepidopteran) that does not reflect the simple combination of the spectrum exhibited by each insect inhibitory agent alone (i.e., the combination of Lepidopteran insect inhibition provided by one agent and Lepidopteran insect inhibition provided by another agent).

In certain embodiments, multi-domain toxin proteins can be constructed by operable linkage of a polynucleotide encoding a first *Bacillus thuringiensis* insect inhibitory protein comprising a domain I, a domain II and a first domain III region with a polynucleotide encoding a supplemental Cry protein domain III region which may be the same as the first domain III or obtained from a distinct second *Bacillus thuringiensis* crystal protein different from the first. In certain embodiments, the *Bacillus thuringiensis* insect inhibitory protein is a Cry1, a Cry2, or a Cry3 insect inhibitory protein.

In certain embodiments, the chimeras of the present invention can further comprise at their C-terminal ends a protoxin domain. Such protoxin domains can be obtained from any of: i) the same Cry1-Cry9-type or other three domain Cry protein (if available, Cry2 and Cry3 type proteins lack such protoxin domains) as the N-terminal domain I, II, and first domain III regions of the multi-domain toxin; ii) from a Cry1-type protein that is distinct from the N-terminal domain I, II, and first domain III region Cry1-type protein; or iii) from the same parent protein as the supplemental Cry protein domain III region of the multi-domain toxin.

Operable linkage of the supplemental Cry protein domain III to domains I, II, and III of the Cry1-type, Cry2-type, or Cry3-type protein can be achieved in any manner that provides for a composite multi-domain toxin protein that exhibits insect inhibitory activity. In certain embodiments, the supplemental Cry protein domain III region directly abuts either the N- or C-terminus of the Cry1-type, Cry2-type, or Cry3-type domain III region. In other embodiments, the supplemental Cry protein domain III region is operably linked to the N- or C-terminus of the Cry1-type, Cry2-type, or Cry3-type domain III region by one, two, three, or more spacer amino acid residues. Spacer amino acids can be derived from any source. In certain embodiments, the spacer amino acids that operably link the supplemental Cry protein domain III region to the Cry1-type, Cry2-type, or Cry3-type domain III region can comprise a one or more amino acid residues that function as a flexible protein hinge region. Protein hinge regions can be obtained from known hinge regions or can be synthetic. Hinge regions of various proteins have been identified and, in certain non-limiting and exemplary embodiments, can comprise serine and glycine residues (Flores et al., BMC Bioinformatics 8:167, 2007). Synthetic hinge regions include, but are not limited to, Ser-Gly-Gly-Ser-Gly (SGGSG) peptides, one or more Gly residue(s), Gly-Ser-Gly (GSG), Gly-Ser-Gly-Ser-Gly (GSGSG), and various permutations of glycine and/or serine.

Approximate boundaries of the domain regions of exemplary and non-limiting Cry1-type, Cry2-type, or Cry3-type proteins are described herein. In certain embodiments provided herein, domain I, domain II, and/or domain III in any particular Cry1-type, Cry2-type, or Cry3-type protein can comprise any of one, two, three, four, five, six, seven, or more additional residues on either the N-terminal end or C-terminal end of the domain. In certain embodiments provided herein, domain I, domain II, and/or domain III in any particular Cry1-type, Cry2-type, or Cry3-type protein can also comprise any of one, two, three, four, five, six, seven, or fewer residues on either the N-terminal end or C-terminal end of the domain.

In considering any of the foregoing methods, it is further contemplated that the amino terminal and carboxy terminal boundaries of the domain regions Cry1 and Cry2-type proteins correspond to: for domain I, from about amino acid residues 1-33 at the amino terminus to about amino acid residues 214-224 at the carboxy terminus; for domain II, from about amino acid residues 224-228 at the amino terminus to about amino acid residues 413-439 at the carboxy terminus; and for domain III, from about amino acid residues 425-450 at the amino terminus to about amino acid residues 560-582 at the carboxy terminus. However, it is contemplated that the absolute boundary of domain I, domain II, and/or domain III in any particular Cry1 protein can vary by any of one, two, three, four, five, six, seven, or more additional or fewer residues on either the N-terminal end or C-terminal end of the range of indicated residues. Thus, it is not necessary to join the various domains at any exact boundary residues specified in order to obtain an insect inhibitory multi-domain toxin protein. In one exemplary embodiment, a supplementary Cry protein domain III of a Cry1F protein toxin was operably linked to the carboxy terminus of domain III of a Cry1Ac protein by insertion of the supplementary Cry1F domain III coding region between the C-terminal end of the Cry1Ac domain III coding region and the N-terminal end of the Cry1Ac protoxin domain coding region to yield a TIC465-type multi-domain protein (SEQ ID NO:1) that is encoded by SEQ ID NO:2. In another exemplary embodiment, a supplementary Cry protein domain III of a Cry2Ab was operably linked to carboxy terminus of a domain III of a Cry1Ac toxin protein by insertion of the supplementary Cry2Ab domain III coding region between the C-terminal end of the Cry1Ac domain III coding region and the N-terminal end of the Cry1Ac protoxin domain coding region to yield a TIC467-type multi-domain protein (SEQ ID NO:3) that is encoded by SEQ ID NO:4. In another exemplary embodiment, a supplementary Cry protein domain III of a Cry3Bb was operably linked to the carboxy terminal end of domain III of a Cry1Ac protein by insertion of the supplementary Cry3Bb domain III coding region between the C-terminal end of the Cry1Ac domain III coding region and the N-terminal end of the Cry1Ac protoxin domain coding region to yield a TIC469-type multi-domain protein (SEQ ID NO:5) that is encoded by SEQ ID NO:6. It is further contemplated that residues from a junction region (i.e. the junction of the supplementary domain III with the domain III of the Cry1A-type protoxin) can be derived from either parent molecule so long as the amino residues at the junction are either similar to the amino acids of the other parent molecule, substitutable for the amino acids of the other parent molecule so that they do not adversely effect insect inhibitory activity of the resultant multi-domain toxin protein, and/or are substitutable for the amino acids of the other parent molecule in that they do not disrupt secondary structural elements present at the junctions that include, but are not limited to, alpha-helices or beta-strands found in the respective domains. It is also contemplated that wholly synthetic residues that are not found in either parent molecule can be used to form the junctions between domains so long as the amino residues at the junction are either similar to the amino acids of the other parent molecule, substitutable for the amino acids of the other parent molecule in that they do not adversely effect insect inhibitory activity of the resultant multi-domain toxin protein, and/or are substitutable for the amino acids of the other parent molecule in that they do not disrupt secondary structural elements present at the junctions that include, but are not limited to, alpha-helices or beta-strands found in the respective domains. In certain embodiments, the synthetic residues that form the junction between the supplementary Cry protein domain III regions can comprise a protein hinge region.

In one embodiment, the multi-domain toxin proteins comprise insect inhibitory proteins referred to herein as "TIC465-type" proteins that comprise, from their N- to C-terminus, domains I, II, and III of a Cry1Ac protein followed by a supplementary operably linked C-terminal Cry1F domain III. In certain embodiments, such multi-domain toxin TIC465-type proteins can further comprise at their C-terminal end a Cry1A protoxin domain. An exemplary and non-limiting, TIC465-type multi-domain toxin protein that further comprises the Cry1Ac protoxin domain at its C-terminus is provided herein as SEQ ID NO:1. In certain embodiments, the TIC465-type multi-domain toxin proteins comprise insect inhibitory proteins that have at least 70%, 80%, 85%, 88%, 90%, 95%, 98%, 99% or 100% sequence identity to SEQ ID NO:1 or to residues 1 to 754 of SEQ ID NO:1. TIC465-type multi-domain toxin proteins which exhibit at least 70%, 80%, 85%, 88%, 90%, 95%, 98%, 99% or 100% amino acid sequence identity to residues 1 to 754 sequence of SEQ ID NO:1 that also exhibit insect inhibitory activity against *Ostrinia* sp., *Helicoverpa* sp., *Agrotis* sp., *Spodoptera* sp., and/or *Striacosta* sp. are also provided. Insect inhibitory fragments of TIC465-type multi-domain toxins include, but are not limited to, any one of or any combination of: i) proteins comprising a complete, partial, or internal deletion of the C-terminal protoxin domain of SEQ ID NO:1; ii) N-terminal deletions of about 1 to about 3, about 1 to about 5, about 1 to about 10, about 1 to about 20, or about 1 to about 30 amino acid residues of SEQ ID NO:1; and/or iii) C-terminal deletions of about 1 to about 3, about 1 to about 5, about 1 to about 10, amino acid residues of a protein comprising residues 1 to 754 of SEQ ID NO:1. Nucleic acids encoding any of the aforementioned TIC465-type multi-domain toxins are also provided.

In another embodiment, the multi-domain toxin proteins comprise insect inhibitory proteins referred to herein as "TIC467-type" proteins that comprise, from their N- to C-terminus, domains I, II, and III of a Cry1Ac protein followed by a supplementary operably linked C-terminal Cry2Ab domain III. In certain embodiments, such multi-domain toxin TIC467-type proteins can further comprise at their C-terminal end a Cry1A protoxin domain. In an exemplary embodiment, TIC467-type multi-domain toxin protein that further comprises the Cry1Ac protoxin domain at its C-terminus is provided herein as SEQ ID NO:3. In certain embodiments, the TIC467-type multi-domain toxin proteins comprise insect inhibitory proteins that have at least 70%, 80%, 85%, 88%, 90%, 95%, 98%, 99% or 100% sequence identity to SEQ ID NO:3 or to residues 1 to 774 of SEQ ID NO:3. TIC467-type multi-domain toxin proteins which exhibit at least 70%, 80%, 85%, 88%, 90%, 95%, 98%, 99% or 100% amino acid sequence identity to residues 1 to 774 sequence of SEQ ID NO:3 that also exhibit insect inhibitory activity against *Ostrinia* sp., *Helicoverpa* sp., *Agrotis* sp., *Spodoptera* sp., and/or *Striacosta* sp. are also provided. Insect inhibitory fragments of TIC467-type multi-domain toxins include, but are not limited to, any one of or any combination of: i) proteins comprising a complete, partial, or internal deletion of the C-terminal protoxin domain of SEQ ID NO:3; ii) N-terminal deletions of about 1 to about 3, about 1 to about 5, about 1 to about 10, about 1 to about 20, or about 1 to about 30 amino acid residues of SEQ ID NO:3; and/or iii) C-terminal deletions of about 1 to about 3, about 1 to about 5, about 1 to about 10, amino acid residues of a protein comprising residues 1 to 774 of SEQ ID NO:3. Nucleic acids encoding any of the aforementioned TIC467-type multi-domain toxins are also provided.

In another embodiment, the multi-domain toxin proteins comprise insect inhibitory proteins referred to herein as "TIC469-type" proteins that comprise, from their N- to C-terminus, domains I, II, and III of a Cry1Ac protein followed by a supplementary operably linked C-terminal Cry3Bb domain III. In certain embodiments, such multi-domain toxin TIC469-type proteins can further comprise at their C-terminal end a Cry1A protoxin domain. In an exemplary embodiment, TIC469-type multi-domain toxin protein that further comprises the Cry1Ac protoxin domain at its C-terminus is provided herein as SEQ ID NO:5. In certain embodiments, the TIC469-type multi-domain toxin proteins comprise insect inhibitory proteins that have at least 70%, 80%, 85%, 88%, 90%, 95%, 98%, 99% or 100% sequence identity to SEQ ID NO:5 or to residues 1 to 756 of SEQ ID NO:5. TIC469-type multi-domain toxin proteins which exhibit at least 70%, 80%, 85%, 88%, 90%, 95%, 98%, 99% or 100% amino acid sequence identity to residues 1 to 756 sequence of SEQ ID NO:5 and that also exhibit insect inhibitory activity against *Ostrinia* sp., *Helicoverpa* sp., *Agrotis* sp., *Spodoptera* sp., and/or *Striacosta* sp. are also provided. Insect inhibitory fragments of TIC469-type multi-domain toxins include, but are not limited to, any one of or any combination of: i) proteins comprising a complete, partial, or internal deletion of the C-terminal protoxin domain of SEQ ID NO:5; ii) N-terminal deletions of about 1 to about 3, about 1 to about 5, about 1 to about 10, about 1 to about 20, or about 1 to about 30 amino acid residues of SEQ ID NO:5; and/or iii) C-terminal deletions of about 1 to about 3, about 1 to about 5, about 1 to about 10, amino acid residues of a protein comprising residues 1 to 756 of SEQ ID NO:5. Nucleic acids encoding any of the aforementioned TIC469-type multi-domain toxins are also provided.

Peptides, polypeptides, and proteins biologically functionally equivalent to multi-domain toxin include, but are not limited to, amino acid sequences containing conservative amino acid substitutions in the multi-domain toxin protein sequences. An example of multi-domain toxin proteins that can be substituted to obtain biological equivalents include, but are not limited to, a multi-domain toxin protein sequence of any one of SEQ ID NOs: 1, 3, 5, or an insect inhibitory fragment thereof. In such amino acid sequences, one or more amino acids in the sequence is (are) substituted with another amino acid(s), the charge and polarity of which is similar to that of the native amino acid, i.e., a conservative amino acid substitution, resulting in a silent change.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

EXAMPLES

The following disclosed embodiments are merely representative of the invention, which may be embodied in various forms. Thus, specific structural and functional details disclosed herein are not to be interpreted as limiting.

Example 1

Construction of the Novel, Synthetic Lepidopteran-Active Insect Toxin Coding Sequences Encoding the Proteins, TIC465, TIC467 and TIC469.

Coding sequences, encoding novel, chimeric insect toxin proteins were constructed using methods well known in the art such as polymerase chain reaction and restriction endonuclease digestion-based cloning. Each novel toxin coding sequence provided below was constructed using a Cry1Ac coding sequence in which an additional domain III from a different toxin molecule coding sequence was inserted in between the domain III and protoxin domain of the Cry1 coding sequence. The novel insect toxin molecule TIC465 protein sequence is presented as SEQ ID NO:1 and is encoded by the coding sequence presented as SEQ ID NO:2. It is comprised of a Cry1 coding sequence in which domain III of Cry1F is inserted between the domain III and protoxin domain of the Cry1Ac coding sequence. The novel insect toxin molecule TIC467 protein sequence is presented as SEQ ID NO:3 and is encoded by the coding sequence presented as SEQ ID NO:4. It is comprised of a Cry1 coding sequence in which domain III of Cry2Ab is inserted between the domain III and protoxin domain of the Cry1Ac coding sequence. The novel insect toxin molecule TIC469 protein sequence is presented as SEQ ID NO:5 and is encoded by the coding sequence presented as SEQ ID NO:6. It is comprised of a Cry1 coding sequence in which domain III of Cry3Bb is inserted between the domain III and protoxin domain of the Cry1Ac coding sequence. Each novel insect toxin protein described in this example provides improved insecticidal properties over those known in the art and is demonstrated in examples 2 through 5.

Example 2

TIC465, TIC467 and TIC469 Demonstrate Improved and Novel Toxicity Against Lepidopteran Pests This example illustrates the toxicity of the TIC465, TIC467 or TIC469 insect toxin proteins when provided in an insect diet and fed to Black Cutworm (BCW, *Agrotis ipsilon*), Corn Earworms (CEW, *Helicoverpa zea*), European Corn Borers (ECB, *Ostrinia nubilalis*), Western Bean Cutworms (WBC, *Striacosta albicosta*) and Fall Armyworms (FAW, *Spodoptera frugiperda*).

The coding sequence encoding the TIC465, TIC467 or TIC469 toxin proteins (presented as SEQ ID NOS:2, 4 and 6, respectively) were cloned into a bacterial expression vector. The resulting vector was used to transform *Bacillus thuringiensis* strain, EG10650 by electroporation. The transformed cells were grown in C2 medium for 3 days at 30 degrees Celsius. After 3 days of growth, most of the culture had lysed as is expected in Bt cultures. The lysed cell preparation was treated with Benzonase™ (Novagen; 12.5 U/ml sample) to reduce sample viscosity. PMSF (100 mM Phenylmethanesulfonyl fluoride in Isopropylalcohol) was added to the suspension to a final concentration of 0.1 mM and allowed to incubate for one hour at 30 degrees Celsius. The suspension was then centrifuged at 2500×g for 10 min. The supernatant was discarded and the pellet re-suspended in 5 mL TX buffer (10 mM Tris/HCl, 0.005% Triton X-100, pH 7.5) and centrifuged again. The supernatant was discarded and the pellet was re-suspended again in another 5 ml of TX buffer. The resulting Bt spore/crystal mixtures containing the toxin protein in TX buffer was analyzed by SDS-PAGE and quantified using spot densitometry.

Bt spore/crystal mixtures were submitted for insect diet-overlay bioassays against the following insects: Black Cutworm (BCW, *Agrotis ipsilon*), Corn Earworms (CEW, *Helicoverpa zea*), European Corn Borers (ECB, *Ostrinia nubilalis*), Western Bean Cutworms (WBC, *Striacosta albicosta*) and Fall Armyworms (FAW, *Spodoptera frugiperda*) in 96-well format. Southland Multiple Species Lepidopteran diet (Southland Products, Lake Village, Ark.) was dispensed into 96-well Falcon round bottom plates with 200 microliters of diet per well. Protein samples in buffer were overlaid on top of the diet using 20 microliters of sample per well. Typically twenty four wells were treated with each dose. The sample overlay was allowed to dry before target insects were added to the well. In the case of ECB, FAW and WBC, one insect neonate per well was added to the plates before covering with a perforated plastic seal. In the case of ECB and WBC, one insect neonate per well was added to the plates before covering with a perforated plastic seal. In the case of CEW and first instar BCW, eggs suspended in 0.2% agar were dispensed into the wells. The wells were again dried before covering the plate with a perforated plastic seal. The bioassay plates were incubated for five days with neonate infested plates or for six days with egg overlay infestations. Plates were placed in an incubator set to 27 degrees Celsius with no light cycle at 60% relative humidity. After the requisite incubation period, the wells were assessed for mortality and stunting. Bioassays were repeated several times for consistency in the analysis using a variety of concentrations to determine the minimal amount of toxin required to cause significant mortality ($p<0.0001$). The insect toxin Cry1Ac (presented as SEQ ID NO:7 and encoded by SEQ ID NO:8) was used for comparison in each bioassay. Table 1 illustrates the amount of TIC465, TIC467 or TIC469 required to cause significant mortality ($p<0.0001$) when provided in an insect diet and fed to Black Cutworm (BCW, *Agrotis ipsilon*), Corn Earworms (CEW, *Helicoverpa zea*), European Corn Borers (ECB, *Ostrinia nubilalis*), Western Bean Cutworms (WBC, *Striacosta albicosta*) and Fall Armyworms (FAW, *Spodoptera frugiperda*). Since each toxin is greater in size relative to the Cry1Ac control, the values presented below are expressed in molarity to demonstrate the improved properties observed for each chimeric toxin molecule.

TABLE 1

TIC465, TIC467 and TIC469 toxin mortality ($p<0.0001$) to Black Cutworm (BCW, *Agrotis ipsilon*), Corn Earworms (CEW, *Helicoverpa zea*), European Corn Borers (ECB, *Ostrinia nubilalis*), Western Bean Cutworms (WBC, *Striacosta albicosta*) and Fall Armyworms (FAW, *Spodoptera frugiperda*)

| Toxin | BCW (moles/liter) | ECB (moles/liter) | CEW (moles/liter) | FAW (moles/liter) | WBC (moles/liter) |
|---|---|---|---|---|---|
| Cry1Ac | $1.5 \times 10^{-7}$ | $9.4 \times 10^{-10}$ | $1.5 \times 10^{-8}$ | $1.9 \times 10^{-7}$ | $7.5 \times 10^{-6}$ |
| TIC465 | $1.7 \times 10^{-8}$ | $4.2 \times 10^{-10}$ | $7.4 \times 10^{-9}$ | $1.7 \times 10^{-7}$ | $6.7 \times 10^{-8}$ |
| TIC467 | $1.3 \times 10^{-7}$ | $3.3 \times 10^{-7}$ | $7.3 \times 10^{-9}$ | $3.3 \times 10^{-7}$ | $3.3 \times 10^{-7}$ |
| TIC469 | $1.7 \times 10^{-7}$ | $6.7 \times 10^{-10}$ | $1.3 \times 10^{-8}$ | $3.3 \times 10^{-7}$ | $3.3 \times 10^{-7}$ |

As can be seen in Table 1 above, TIC465 demonstrates superior control over Cry1Ac when presented in the diet of BCW, CEW, and WBC. There is approximately a 100 fold reduction in the amount of TIC465 insect toxin protein required to control WBC relative to Cry1Ac and an approximately 10 fold reduction in the amount of TIC465 insect toxin protein required to control BCW and CEW relative to Cry1Ac. With respect to ECB and FAW equivalent or slightly less amounts of TIC465 is required to provide significant control relative to Cry1Ac. The TIC467 chimeric toxin molecule shows improved performance against CEW relative to Cry1Ac, requiring approximately 10 fold less toxin to cause significant mortality. With respect to BCW, FAW and WBC TIC467 and Cry1Ac require similar levels of toxin to cause significant mortality. TIC467 is less effective than Cry1Ac in causing mortality to ECB. The amount of TIC469 insect toxin required to cause significant mortality in BCW, ECB, CEW and FAW is approximately the same as that of Cry1Ac. There is an approximately 10 fold reduction in the amount of TIC469 toxin required to cause significant mortality in WBC relative to Cry1Ac.

Each novel chimeric toxin, TIC465, TIC467 and TIC469 was constructed using a Cry1Ac coding sequence in which an additional domain III from a different toxin molecule coding sequence was inserted in between the domain III and protoxin domain of the Cry1 coding sequence. The novel insect toxin molecule TIC465 protein sequence is comprised of a Cry1Ac coding sequence in which domain III of Cry1F is inserted between the domain III and protoxin domain of the Cry1 Ac coding sequence. The novel insect toxin molecule TIC467 protein sequence is comprised of a Cry1Ac coding sequence in which domain III of Cry2Ab is inserted between the domain III and protoxin domain of the Cry1Ac coding sequence. The novel insect toxin molecule TIC469 protein sequence is comprised of a Cry1Ac coding sequence in which domain III of Cry3Bb is inserted between the domain III and protoxin domain of the Cry1Ac coding sequence.

The addition of a supplemental domain III from another insect toxin, inserted between the domain III and protoxin domain of the parent molecule Cry1Ac, results in many cases in improved toxicity to specific insects while maintaining an equivalent or lower level of toxicity to other insects susceptible to Cry1Ac.

The novel chimeric insect toxin molecules, TIC465, TIC467 and TIC469 may provide an alternative mode of action against the insect species that is operatively different from the mode of action of the parent Cry1Ac molecule due to the introduction of a supplemental domain III within the toxin molecule composition. Therefore, the production of chimeric toxin molecules containing a supplemental domain III of the same or different insect toxin molecule inserted between the domain III and protoxin domain of the parent molecule may provide a different or novel mode of action against the insect species. This different or novel property will be useful in strategies in which multiple modes of control of an insect species are desirable. For the purpose of providing multiple insect toxin coding sequences for expression in transformed plants, coding sequences can be designed for expression in plants in which each coding sequence is sufficiently different to prevent recombination from occurring during transformation or crossing of transformed lines. For example, a plant can be transformed with an expression cassette containing a plant codon designed Cry1Ac coding sequence and another plant transformed with an expression cassette containing a plant codon designed TIC465 coding sequence. Each coding sequence encodes a Cry1Ac molecule wherein the TIC465 coding sequence has a supplemental domain III of another insect toxin molecule inserted between the domain III and protoxin domain of Cry1Ac. The Cry1Ac portion of the TIC465 toxin coding sequence can be designed to be divergent enough from the Cry1Ac toxin coding sequence to prevent recombination from occurring. Both transformed plants can therefore be crossed to provide a resulting progeny plant expressing both the Cry1Ac and TIC465 insect toxin molecules, providing enhanced control with potentially two modes of action against the insect species. Alternatively, a single plant can be transformed with both Cry1 Ac and TIC465 expression cassettes to provide enhanced control with potentially two modes of action against an insect species.

Example 3

Synthesis of Genes Encoding a TIC465, TIC467 or TIC469 Protein and Expression Cassettes for Expression in Plants Nucleotide sequences encoding TIC465, TIC467 or TIC469 proteins (SEQ ID NOS: 1, 3 and 5, respectively) is designed and synthesized. For example, a non-native coding region designed for plant expression of TIC465 is provided here as TIC465nno (SEQ ID NO:9). The synthetic TIC465nno coding sequence is characterized by a lower A+T content than the native coding regions that was derived from *Bacillus thuringiensis* and used to construct the chimeric toxin molecule coding sequence, eliminating regions of the native sequences that are A+T rich and replacing those with sequences that have fewer A+T residues. Similarly, non-native coding sequences can be designed for a TIC467nno or TIC469nno coding sequence for expression in plants.

A variety of plant expression cassettes can be constructed with the non-native TIC465nno coding sequence (SEQ ID NO:9). Such expression cassettes are useful for transient expression in plant protoplasts or transformation of plant cells. Typical expression cassettes are designed with respect to the eventual placement of the protein within the cell. One set of expression cassettes is designed in a manner to allow the protein to be translated and remain in the cytosol. Another set of expression cassettes is designed to have a transit peptide contiguous with the toxin protein to allow targeting to an organelle of the cell such as the chloroplast or plastid. All expression cassettes are designed to begin at the 5' end with a promoter which can be comprised of multiple promoter elements and enhancer elements contiguously linked to boost the expression of the transgene. The promoter sequence is usually followed contiguously with one or more leader sequences 3' to the promoter. An intron sequence is often provided 3' to the leader sequence to improve expression of the transgene. A coding sequence for the toxin or transit peptide and coding sequence for the toxin is located 3' of the promoter, leader and intron configuration. A terminator sequence is provided 3' of the coding sequence to facilitate termination of transcription and provides sequences important for the polyadenylation of the resulting transcript. All of the elements described above are arranged contiguously with often additional sequence provided for the construction of the expression cassette such as restriction endonuclease sites or ligation independent cloning sites.

A set of expression cassettes designed for cytosolic expression and plastid targeted expression of the insect toxin protein are described herein. A first expression cassette used for the expression of the TIC465 toxin protein for cytosolic expression is presented as SEQ ID NO:10. The cassette is comprised in the 5' to 3' direction of a Cauliflower mosaic virus 35S enhanced promoter and leader, operably linked to a *Triticum aestivum* Lhcb1 leader, which is in turn operably linked to a *Oryza sativa* actin 1 intron, which in turn is linked to the TIC465nno coding sequence and which is finally operably linked to a *Triticum aestivum* Hsp17 terminator. A second expression cassette is designed for plastid targeted expression of the TIC465 toxin protein in which an N-terminal *Arabidopsis* shkG chloroplast peptide encoding sequence (i.e. CTP2) is fused in frame to the non-native TIC465nno coding sequence. The sequences encoding the CTP2-TIC465nno plastid targeted toxin protein (SEQ ID NO:11) is presented as SEQ ID NO:12. The plastid targeted expression cassette is presented as SEQ ID NO:13. The cassette is comprised in the 5' to 3' direction of a Cauliflower mosaic virus 35S enhanced promoter and leader, operably linked to a *Triticum aestivum* Lhcb1 leader, which is in turn operably linked to a *Oryza sativa* actin 1 intron, which in turn is linked to the CTP2-TIC465nno coding sequence and which is finally operably linked to a *Triticum aestivum* Hsp17 terminator. A similar set of expression cassettes can be designed to express a TIC467nno, CTP2-TIC467nno, TIC469nno or CTP2-TIC469nno coding sequence.

Example 4

Construction of *Agrobacterium*-Mediated Transformation Vectors Containing a TIC465, TIC467 or TIC469 Expression Cassette and Transfer to *Agrobacterium*

To construct *Agrobacterium* mediated transformation vectors, the TIC465nno, TIC467nno and TIC469nno expression cassettes are cloned into suitable vectors between the *Agrobacterium* border sequences such that they would be transferred to the genome of a host plant cell by suitable disarmed *Agrobacterium* hosts comprising the constructed vectors along with a selectable marker gene. More specifically, the restriction fragment containing the entire cytosolic expression cassette for expression of a TIC465nno coding sequence (SEQ ID NO:10) is cloned into an *Agrobacterium* plant transformation vector. Similarly, the restriction fragment containing the entire plastid targeted expression cassette for a CTP2-TIC465nno (SEQ ID NO:13) is cloned into an *Agrobacterium* plant transformation vector. The vectors containing the TIC465nno or CTP2-TIC465nno expression cassettes (i.e., untargeted cassette or targeted cassette) are introduced into *Agrobacterium* by electroporation or by tri-parental mating. A similar set of binary vectors containing expression cassettes for expression of a TIC467nno, CTP2-TIC467nno, TIC469nno or CTP2-TIC469nno coding sequence can be produced as described above.

Example 5

In Planta Testing of TIC465, TIC467 or TIC469 for Control of Lepidopteran Pests

This example illustrates the toxicity of the TIC465, TIC467 or TIC469 insect toxin proteins to Black Cutworms (BCW, *Agrotis ipsilon*), Corn Earworms (CEW, *Helicoverpa zea*), European Corn Borers (ECB, *Ostrinia nubilalis*), Western Bean Cutworms (WBC, *Striacosta albicosta*) and Fall Armyworms (FAW, *Spodoptera frugiperda*) when expressed in plant tissue and presented in the insect diet. Corn plant tissue is transformed with a TIC465nno, CTP2-TIC465nno, TIC467nno, CTP2-TIC467nno, TIC469nno or CTP2-TIC469nno expression cassette described above. The transformed tissue is selected by methods well known in the art and allowed to regenerate into whole plants. By approximately V3 to V8 stage of the R0 plant development, the plants will be ready for use in insect testing. Whole plants or young leaf tissue expressing the TIC465nno, TIC467nno or TIC469nno toxin protein is infested with Black Cutworms (BCW, *Agrotis ipsilon*), Corn Earworms (CEW, *Helicoverpa zea*), European Corn Borers (ECB, *Ostrinia nubilalis*), Western Bean Cutworms (WBC, *Striacosta albicosta*) or Fall Armyworms (FAW, *Spodoptera frugiperda*) and allowed to feed on the plant tissue from one to several days. Control plants using the same variety of corn plant that was used in the transformation but not having been transformed with a TIC465nno, TIC467nno or TIC469nno insect toxin protein are infested as well. The insect larvae are weighed prior to infestation to provide a baseline measurement of their size. After a specified infestation period, the insects are recovered and weighed. In addition, the quantities of living and dead insects are determined. In some cases, all insects will be killed by feeding upon the plants expressing the TIC465nno, TIC467nno, or TIC469nno toxin protein. In other cases, some insects will remain alive; however there will be a noticeable reduction in growth relative to the control plant infestations.

Further testing can be conducted in plants derived from crosses of selected transformed events to provide more precise information regarding the performance of the insect toxins, TIC465nno, TIC467nno and TIC469nno with respect to transgene copy number. R0 transformed events are selected based upon the presence of a single-copy of the TIC465nno, CTP2-TIC465nno, TIC467nno, CTP2-TIC467nno, TIC469nno or CTP2-TIC469nno transgene cassette using methods known in the art. The selected R0 transformed events are crossed with a non-transformed corn variety to produce F1 progeny. The F1 progeny are grown and tested for the presence of the TIC465nno, CTP2-TIC465nno, TIC467nno, CTP2-TIC467nno, TIC469nno or CTP2-TIC469nno transgene cassette using methods known in the art. By approximately V3 to V8 stage of the F1 plant development, the plants will be ready for use in insect testing. Whole plants or young leaf tissue expressing a TIC465, TIC467 or TIC469 toxin protein is infested with Black Cutworms (BCW, *Agrotis ipsilon*), Corn Earworms (CEW, *Helicoverpa zea*), European Corn Borers (ECB, *Ostrinia nubilalis*), Western Bean Cutworms (WBC, *Striacosta albicosta*) and Fall Armyworms (FAW, *Spodoptera frugiperda*) and allowed to feed on the plant tissue from one to several days. Control plants using the same variety of corn plant that was used in the transformation but not having been transformed with a TIC465, TIC467 or TIC469 insect toxin protein are infested as well. The insect larvae are weighed prior to infestation to provide a baseline measurement of their size. After a specified infestation period, the insects are recovered and weighed. In addition, the quantities of living and dead insects are determined. In some cases, all insects will be killed by feeding upon the plants expressing a TIC465, TIC467 or TIC469 toxin protein. In other cases, some insects will remain alive; however there will be a noticeable reduction in growth relative to the control plant infestations. The level of expression of a TIC465, TIC467 or TIC469 toxin protein expressed in the tissue presented to the insect can be determined using ELISA with antibodies directed against a TIC465, TIC467 or TIC469 toxin protein. Alternatively, antibodies directed against the parent polypeptide molecules to a TIC465, TIC467 or TIC469, the Cry1Ac toxin polypeptide molecule and/or the supplemental Cry protein domain III polypeptide molecule, may be used for quantification. In certain embodiments, epitopes present on the Cry1Ac toxin and/or the supplemental Cry protein domain III molecules responsible for stimulating antibody production in mammals are presented by a TIC465, TIC467 or TIC469 toxin molecule.

Example 6

Insect Control Using TIC465, TIC467 and/or TIC469 in Combination with Other Insect Control Agents This example illustrates several methods by which increased resistance to a specific insect pest or broader resistance to several classes of insect pests can be achieved to provide greater insect protection for a crop plant. All of the strategies described below can also be used to enhance an insect resistance management program.

I) Combination of TIC465, TIC467 or TIC469 with Insect Inhibitory dsRNA Molecules in Plants Double stranded RNA mediated gene suppression of biological function within target insect pests can be combined with genes encoding a TIC465, TIC467 or TIC469 protein. Insect genes that perform key biological functions that can be targeted by dsRNA are described in PCT Patent Application Publication No. WO 2005/110068 and U.S. Patent Application Publication No. 2006/0021087. Homologs of genes described in these publications can be identified in any target insect pest desired for control and can be sequences derived from Lepidopteron species, Hemipteran species, Coleopteran species or any other order of insect that is identified as an agronomic pest. Expression of dsRNA molecules is achieved by recovery of transgenic plants comprising a promoter active in those plants that is operably linked to fragments of the target pest sequence of at least 19-24 nucleotides in length and the reverse complements of those sequences. For example, for the control of Black cutworm (*Agrotis ipsilon*), Corn Earworm (*Helicoverpa zea*) and European Corn Borer (*Ostrinia nubilalis*) dsRNA molecules derived from sequences encoding a V-ATPase A subunit molecule, presented as SEQ ID NOS: 146, 147 and 148, respectively in PCT Patent Application Publication No. WO 2005/110068 can be expressed in plant tissues expressing a TIC465, TIC467 or TIC469 toxin protein to achieve greater levels of control of the insect pest. The combination of an insect toxin protein with a dsRNA can provide synergistic control greater than the sum of each control agent presented individually in transformed plants.

II) Combination of TIC465, TIC467 or TIC469 with Insect Inhibitory Proteins Other than TIC465, TIC467 or TIC469 in Plants Methods of obtaining transgenic plants that express Lepidopteran-active proteins such as Cry1A proteins (U.S. Pat.

No. 5,880,275), Cry1B (U.S. patent application Ser. No. 10/525,318), Cry1C (U.S. Pat. No. 6,033,874), Cry1F, VIP proteins and VIP protein chimeras constructed using portions of crystalline Bt proteins, Cry1A/F chimeras (U.S. Pat. Nos. 7,070,982, 6,962,705, and 6,713,063), and a Cry2Ab protein (U.S. Pat. No. 7,064,249) are well characterized. Plants expressing both a TIC465, TIC467 or TIC469 protein and another Lepidopteran active protein can be obtained by making crosses of individual transgenic plants that express a TIC465, TIC467 or TIC469 and individual transgenic plants that express the other Lepidopteran proteins. Alternatively, plant transformation vectors that provide for expression of a TIC465, TIC467 or TIC469 and another Lepidopteran active protein can be used to transform plants. The combination of an insecticidal protein or proteins with one or more double stranded RNA, all independently active against a Lepidopteran pest, is preferred as it provides two different modes of action (resistance management), and results in unexpected synergistic effects that are not observed with either the insecticidal protein alone, the double stranded RNA alone, or combinations of two different insecticidal proteins, both active against a Lepidopteran pests, or combinations of two different dsRNA's, both active against a Lepidopteran pests.

In addition, the spectrum of resistance of the crop plant could be broadened to contain resistance to additional orders of insect pests such as Coleopteran, Hemipteran, or Dipteran pests in addition to a Lepidopteran pest using both the expression of insect toxin proteins and double stranded RNA molecules within the plant. Toxin molecules directed towards a Coleopteran pest such as a Cry3Bb (U.S. Pat. No. 6,501,009) can be expressed in plants expressing a TIC465, TIC467 or TIC469 toxin protein to provide control of insect pests affecting plant tissues above and below the ground. A Coleopteran directed dsRNA such as those described in PCT Patent Application Publication No. WO 2005/110068 can also be expressed in addition to the insect toxin molecules providing greater synergistic control of the coleopteran pest. Similarly, a toxin molecule and/or dsRNA which control any non-Lepidopteran pest can be expressed in plants expressing a TIC465, TIC467 or TIC469 toxin protein to provide a greater range of insect pest protection.

III) Combination of TIC465, TIC467 or TIC469 with Insect Inhibitory Agents Provided as Seed Treatments Seeds from transgenic plants expressing a TIC465, TIC467 or TIC469 can be treated with a variety of insect inhibitory agents or other pesticidal agents such as fungicides, bacteriocides and nematocides to provide additional control of insect and other plant pests. Seed treatments can enable one to protect the germinating and emerging seedling from various plant pests to assure proper germination and healthy plants in the initial days of growth. The insect inhibitory agent can be another insect toxin protein, a dsRNA, a protein other than an insect toxin with insect inhibitory properties or an organic chemical pesticide. The seed treatment can also be a fungicide, a bacteriocide or nematocide which provides control of a fungal, bacterial or nematode pest. A nematocide for example could be used in combination with TIC465, TIC467 or TIC469 to provide the above ground part of the plant with protection against Lepidopteron pests while below ground, at the roots, protection is provided against a nematode pest.

The insecticidal or pesticidal agent compound formulation can be applied to seeds by any standard seed treatment methodology, including but not limited to, mixing in a container (e.g., a bottle or bag), mechanical application, tumbling, spraying, or immersion. Combinations of these methods can also be employed. An important consideration in the preparation of seed treatment formulations is that the ingredients be non-phytotoxic to the seed. In addition, colorants are normally added for identification purposes to protect from the direct use of treated seed in human or animal food products. Sticking agents are also commonly used to keep the formulation on the seed during handling, shipping, etc. The insecticidal or pesticidal agent compound formulation can be provided in a polymer matrix, and an agricultural adjuvant. The composition can take a variety of forms, including a liquid suspension, a wettable powder, a granule, a water-dispersible granule, a suspension concentrate, or the like. Seeds can be coated using a variety of methods including imbibition, solid matrix priming, coating, spraying and dusting. Seed treatments can take a variety of forms, including suspension concentrates, solutions, emulsions, powders, granules, as well as using polymeric carriers or stickers. For example, the coating process can comprise spraying a composition comprising the insecticidal or pesticidal agent compound(s) onto the seed while agitating the seed in an appropriate apparatus, such as a tumbler or a pan granulator.

An insect inhibitory agent can be selected from a wide range of pyrethroids and other insecticides, and especially including those having low water solubility, low volatility and previously considered to be "non-systemic", are capable of providing protection against shoot/foliar feeding pests to provide both below ground and above ground control of an insect pest. Pesticides suitable for use as seed treatments for insect control include compounds selected from azoles, azines, pyrethrins, pyrethroids, organophosphates, caramoyloximes, pyrroles, pyrazoles, pyridines, amidines, halogenated hydrocarbons and carbamates and combinations and derivatives thereof. Known pesticides within these categories are listed in The Pesticide Manual, 11th Ed., C. D. S. Tomlin, Ed., British Crop Protection Council, Farnham, Surry, UK (1997). The insecticidal, bacteriocidal, fungicidal or nematocidal agent incorporated in the seed treatment must be contained in a formulation that will provide stability to the agent and deliver the agent in a manner consistent with control of the plant pest. The combination of a TIC465, TIC467 or TIC469 with a seed treatment with one or more agents with inhibitory effects to a plant pest or plant pests will provide additional methods of plant pest control.

Various patent and non-patent publications are cited herein, the disclosures of each of which are incorporated herein by reference in their entireties. Documents cited herein as being available from the World Wide Web at certain interne addresses are also incorporated herein by reference in their entireties. Certain biological sequences referenced herein by their "NCBI Accession Number" can be accessed through the National Center of Biotechnology Information on the world wide web at ncbi.nlm.nih.gov.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A polynucleotide which encodes an insect inhibitory protein comprising a Cry1Ac polypeptide, said Cry1Ac polypeptide comprising domains I, II, and III, and a supplemental domain III of a Cry1F, Cry2Ab or Cry3Bb operably linked to domain III of said Cry1Ac polypeptide, and wherein said operable linkage of said supplemental domain III is
   (a) to the N-terminus of said domain III of said Cry1Ac polypeptide; or
   (b) to the C-terminus of said first domain III of said Cry1Ac polypeptide.

2. The polynucleotide of claim 1, wherein said supplemental domain III comprises an amino acid sequence selected from the group consisting of a native Cry1F, Cry2Ab and Cry3Bb domain III polypeptide sequence.

3. The polynucleotide of claim 1, wherein said supplemental domain III comprises an engineered Cry1F, Cry2Ab or Cry3Bb domain III polypeptide sequence, said engineered Cry1F, Cry2Ab or Cry3Bb domain III polypeptide sequence comprising (a) amino acid substitutions, insertions, and/or deletions compared to an amino acid sequence selected from the group consisting of a native Cry1F, Cry2Ab and Cry3Bb domain III polypeptide sequence, wherein said engineered Cry1F, Cry2Ab or Cry3Bb domain III polypeptide sequence is at least 95% sequence identical to the amino acid sequence of its corresponding native sequence, or (b) segments of two or more Cry1F, Cry2Ab or Cry3Bb domain III polypeptide sequences, or (c) amino acid substitutions, insertions, and/or deletions in one or more segments of subpart (b), wherein said segment of said Cry1F, Cry2Ab or Cry3Bb domain III polypeptide sequence is at least 95% sequence identical to its corresponding native segment's sequence.

4. The polynucleotide of claim 1, wherein said supplemental domain III is a Cry1F domain III and wherein said insect inhibitory protein comprises a polypeptide sequence that is at least 95% sequence identical to SEQ ID NO:1.

5. The polynucleotide of claim 4, wherein said insect inhibitory protein exhibits improved insecticidal activity against an *Agrotis*, a *Helicoverpa*, or a *Striacosta* insect relative to a Cry1Ac polypeptide lacking said supplemental domain III.

6. The polynucleotide of claim 1, wherein said supplemental domain III is a Cry2Ab domain III and wherein said insect inhibitory protein comprises a polypeptide sequence that is at least 95% sequence identical to SEQ ID NO:3.

7. The polynucleotide of claim 6, wherein said insect inhibitory protein exhibits improved insecticidal activity against a *Helicoverpa*, or a *Striacosta* insect relative to a Cry1Ac polypeptide lacking said supplemental domain III.

8. The polynucleotide of claim 1, wherein said supplemental domain III is a Cry3Bb domain III and wherein said insect inhibitory protein comprises a polypeptide sequence that is at least 95% sequence identical to SEQ ID NO:5.

9. The polynucleotide of claim 8, wherein said insect inhibitory protein exhibits improved insecticidal activity against a *Striacosta* insect relative to a Cry1Ac polypeptide lacking said supplemental domain III.

10. A transgenic plant comprising the polynucleotide of claim 1.

11. The transgenic plant of claim 10, wherein said plant comprises said insect inhibitory protein at a concentration that inhibits a Lepidopteran insect.

12. The transgenic plant of claim 11, wherein said Lepidopteran insect is an *Agrotis*, a *Helicoverpa*, an *Ostrinia*, a *Striacosta* or a *Spodoptera* insect.

13. A transgenic plant part comprising the polynucleotide of claim 1, wherein said plant part is a leaf, a stem, a flower, a sepal, a fruit, a root, or a seed.

14. A transformed host cell comprising the polynucleotide of claim 1, wherein said host cell is a bacterial cell or a plant cell.

15. The transformed host cell of claim 14, wherein said plant cell is selected from the group consisting of alfalfa, banana, barley, bean, broccoli, cabbage, canola, carrot, cassava, castor, cauliflower, celery, chickpea, citrus, coconut, coffee, corn, clover, cotton, a cucurbit, Douglas fir, eggplant, eucalyptus, flax, garlic, grape, hops, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rye, safflower, shrub, sorghum, Southern pine, soybean, spinach, squash, strawberry, sugar beet, sugarcane, sunflower, sweet gum, sweet potato, switchgrass, tea, tobacco, tomato, triticale, turf grass, watermelon, and wheat plant cells.

16. The transformed host cell of claim 14, wherein said bacterial cell is selected from the group consisting of an *Agrobacterium*, a *Bacillus*, an *Escherichia*, a *Salmonella*, a *Pseudomonas*, and a *Rhizobium* bacterial cell.

17. The transformed host cell of claim 14, wherein said bacterial cell is a *Bacillus thuringiensis* cell.

18. A method for controlling a Lepidopteran insect, said method comprising the steps of:
(a) providing a Lepidopteran insect inhibitory amount of an insect inhibitory protein, wherein said insect inhibitory protein is encoded by the polynucleotide of claim 1; and
(b) contacting said Lepidopteran insect with said inhibitory amount of said insect inhibitory protein, thereby controlling said Lepidopteran insect.

19. The method of claim 18, wherein said Lepidopteran insect is an *Agrotis*, a *Spodoptera*, a *Helicoverpa*, an *Ostrinia*, or a *Striacosta* insect.

20. The method of claim 18, wherein said Lepidopteran insect inhibitory amount of said insect inhibitory protein is provided in a Lepidopteran insect diet in step (a) and said Lepidopteran insect is contacted in step (b) by permitting said Lepidopteran insect to feed on said diet.

21. The method of claim 20, wherein said Lepidopteran insect diet is a transgenic plant, said transgenic plant comprising said polynucleotide.

22. A method for controlling an insect pest, said method comprising the steps of:
(a) providing an insect inhibitory amount of an insect inhibitory protein in combination with an insect control agent that is different from said insect inhibitory protein, wherein said insect inhibitory protein is encoded by the polynucleotide of claim 1; and
(b) contacting said insect pest with said inhibitory amount of said insect inhibitory protein and said insect control agent, thereby controlling said insect pest.

23. The method of claim 22, wherein said insect control agent is selected from the group consisting of an insect inhibitory dsRNA molecule, a Cry1A protein, a Cry1B protein, a Cry1C protein, a Cry1F protein, a VIP protein, a Cry2Ab protein and a Cry3Bb protein.

* * * * *

SEQUENCE LISTING

<160> NUMBER OF SEQ ID NOS: 13

<210> SEQ ID NO 1
<211> LENGTH: 1321
<212> TYPE: PRT
<213> ORGANISM: Artificial sequence
<220> FEATURE:
<223> OTHER INFORMATION: Synthetic

<400> SEQUENCE: 1

```
Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350
```

-continued

```
Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Val Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
            530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
            595                 600                 605

Thr Ala Thr Leu Glu Pro Glu Arg Ile Thr Gln Ile Pro Leu Val Lys
610                 615                 620

Ala His Thr Leu Gln Ser Gly Thr Thr Val Val Arg Gly Pro Gly Phe
625                 630                 635                 640

Thr Gly Gly Asp Ile Leu Arg Arg Thr Ser Gly Gly Pro Phe Ala Tyr
                645                 650                 655

Thr Ile Val Asn Ile Asn Gly Gln Leu Pro Gln Arg Tyr Arg Ala Arg
                660                 665                 670

Ile Arg Tyr Ala Ser Thr Thr Asn Leu Arg Ile Tyr Val Thr Val Ala
            675                 680                 685

Gly Glu Arg Ile Phe Ala Gly Gln Phe Asn Lys Thr Met Asp Thr Gly
690                 695                 700

Asp Pro Leu Thr Phe Gln Ser Phe Ser Tyr Ala Thr Ile Asn Thr Ala
705                 710                 715                 720

Phe Thr Phe Pro Met Ser Gln Ser Ser Phe Thr Val Gly Ala Asp Thr
                725                 730                 735

Phe Ser Ser Gly Asn Glu Val Tyr Ile Asp Arg Phe Glu Leu Ile Pro
                740                 745                 750

Val Thr Leu Glu Ala Glu Tyr Asn Leu Glu Arg Ala Gln Lys Ala Val
            755                 760                 765

Asn Ala Leu Phe Thr Ser Thr Asn Gln Leu Gly Leu Lys Thr Asn Val
770                 775                 780
```

-continued

Thr Asp Tyr His Ile Asp Gln Val Ser Asn Leu Val Thr Tyr Leu Ser
785                 790                 795                 800

Asp Glu Phe Cys Leu Asp Glu Lys Arg Glu Leu Ser Glu Lys Val Lys
            805                 810                 815

His Ala Lys Arg Leu Ser Asp Glu Arg Asn Leu Leu Gln Asp Ser Asn
        820                 825                 830

Phe Lys Asp Ile Asn Arg Gln Pro Glu Arg Gly Trp Gly Gly Ser Thr
    835                 840                 845

Gly Ile Thr Ile Gln Gly Gly Asp Val Phe Lys Glu Asn Tyr Val
850                 855                 860

Thr Leu Ser Gly Thr Phe Asp Glu Cys Tyr Pro Thr Tyr Leu Tyr Gln
865                 870                 875                 880

Lys Ile Asp Glu Ser Lys Leu Lys Ala Phe Thr Arg Tyr Gln Leu Arg
                885                 890                 895

Gly Tyr Ile Glu Asp Ser Gln Asp Leu Glu Ile Tyr Leu Ile Arg Tyr
                    900                 905                 910

Asn Ala Lys His Glu Thr Val Asn Val Pro Gly Thr Gly Ser Leu Trp
            915                 920                 925

Pro Leu Ser Ala Gln Ser Pro Ile Gly Lys Cys Gly Glu Pro Asn Arg
    930                 935                 940

Cys Ala Pro His Leu Glu Trp Asn Pro Asp Leu Asp Cys Ser Cys Arg
945                 950                 955                 960

Asp Gly Glu Lys Cys Ala His His Ser His His Phe Ser Leu Asp Ile
                965                 970                 975

Asp Val Gly Cys Thr Asp Leu Asn Glu Asp Leu Gly Val Trp Val Ile
                    980                 985                 990

Phe Lys Ile Lys Thr Gln Asp Gly His Ala Arg Leu Gly Asn Leu Glu
            995                 1000                1005

Phe Leu Glu Glu Lys Pro Leu Val Gly Glu Ala Leu Ala Arg Val Lys
    1010                1015                1020

Arg Ala Glu Lys Lys Trp Arg Asp Lys Arg Glu Lys Leu Glu Trp Glu
1025                1030                1035                1040

Thr Asn Ile Val Tyr Lys Glu Ala Lys Glu Ser Val Asp Ala Leu Phe
                1045                1050                1055

Val Asn Ser Gln Tyr Asp Gln Leu Gln Ala Asp Thr Asn Ile Ala Met
                    1060                1065                1070

Ile His Ala Ala Asp Lys Arg Val His Ser Ile Arg Glu Ala Tyr Leu
        1075                1080                1085

Pro Glu Leu Ser Val Ile Pro Gly Val Asn Ala Ala Ile Phe Glu Glu
    1090                1095                1100

Leu Glu Gly Arg Ile Phe Thr Ala Phe Ser Leu Tyr Asp Ala Arg Asn
1105                1110                1115                1120

Val Ile Lys Asn Gly Asp Phe Asn Asn Gly Leu Ser Cys Trp Asn Val
            1125                1130                1135

Lys Gly His Val Asp Val Glu Glu Gln Asn Asn Gln Arg Ser Val Leu
        1140                1145                1150

Val Val Pro Glu Trp Glu Ala Glu Val Ser Gln Glu Val Arg Val Cys
    1155                1160                1165

Pro Gly Arg Gly Tyr Ile Leu Arg Val Thr Ala Tyr Lys Glu Gly Tyr
    1170                1175                1180

Gly Glu Gly Cys Val Thr Ile His Glu Ile Glu Asn Asn Thr Asp Glu
1185                1190                1195                1200

Leu Lys Phe Ser Asn Cys Val Glu Glu Glu Ile Tyr Pro Asn Asn Thr

```
                     1205               1210                1215
Val Thr Cys Asn  Asp Tyr Thr Val  Asn Gln Glu Glu  Tyr Gly Gly Ala
             1220                1225                 1230

Tyr Thr Ser Arg  Asn Arg Gly Tyr  Asn Glu Ala Pro  Ser Val Pro Ala
             1235                1240                 1245

Asp Tyr Ala Ser  Val Tyr Glu  Glu  Lys Ser Tyr Thr  Asp Gly Arg Arg
    1250                1255                 1260

Glu  Asn Pro Cys Glu  Phe  Asn Arg Gly Tyr Arg  Asp Tyr Thr Pro Leu
1265                 1270                1275                 1280

Pro Val Gly Tyr  Val Thr Lys Glu  Leu Glu  Tyr Phe Pro Glu  Thr  Asp
             1285                1290                 1295

Lys Val Trp Ile  Glu  Ile Gly Glu  Thr  Glu Gly Thr Phe Ile  Val Asp
             1300                1305                 1310

Ser Val Glu  Leu Leu Leu Met Glu  Glu
        1315                1320

<210> SEQ ID NO 2
<211> LENGTH: 3963
<212> TYPE: DNA
<213> ORGANISM: Artificial sequence
<220> FEATURE:
<223> OTHER INFORMATION: Synthetic

<400> SEQUENCE: 2
atggataaca atccgaacat caatgaatgc attccttata attgtttaag taaccctgaa      60
gtagaagtat taggtggaga agaatagaa  actggttaca ccccaatcga tatttccttg     120
tcgctaacgc aatttctttt gagtgaattt gttcccggtg ctggatttgt gttaggacta     180
gttgatataa tatggggaat ttttggtccc tctcaatggg acgcatttct tgtacaaatt     240
gaacagttaa ttaaccaaag aatagaagaa ttcgctagga accaagccat ttctagatta     300
gaaggactaa gcaatcttta tcaaatttac gcagaatctt ttagagagtg ggaagcagat     360
cctactaatc cagcattaag agaagagatg cgtattcaat tcaatgacat gaacagtgcc     420
cttacaaccg ctattcctct tttggcagtt caaaattatc aagttcctct tttatcagta     480
tatgttcaag ctgcaaattt acatttatca gttttgagag atgtttcagt gtttggacaa     540
aggtggggat tgatgccgc  gactatcaat agtcgttata atgatttaac taggcttatt     600
ggcaactata cagattatgc tgtacgctgg tacaatacgg gattagaacg tgtatgggga     660
ccggattcta gagattgggt aaggtataat caatttagaa gagaattaac actaactgta     720
ttagatatcg ttgctctgtt cccgaattat gatagtagaa gatatccaat tcgtacggtt     780
tcccaattaa caagagaaat ttatacaaac ccagtattag aaaattttga tggtagtttt     840
cgaggctcgg ctcagggcat agaaagaagt attaggagtc cacatttgat ggatatactt     900
aacagtataa ccatctatac ggatgctcat aggggttatt attattggtc agggcatcaa     960
ataatggctt ctcctgtcgg ttttcgggg  ccagaattca cgtttccgct atatggaacc    1020
atgggaaatg cagctccaca acaacgtatt gttgctcaac taggtcaggg cgtgtataga    1080
acattatcgt ccactttata tagaagacct tttaatatag ggataaataa tcaacaacta    1140
tctgttcttg acgggacaga atttgcttat ggaacctcct caaatttgcc atccgctgta    1200
tacagaaaaa gcggaacggt agattcgctg atgaaatac  cgccacagaa taacaacgtg    1260
ccacctaggc aaggatttag tcatcgatta agccatgttt caatgtttcg ttcaggcttt    1320
agtaatagta gtgtaagtat aataagagct cctatgttct cttggataca tcgtagtgct    1380
gaagttaaca atataattgc atcggatagt attactcaaa tccctgcagt gaagggaaac    1440
```

```
tttcttttta atggttctgt aatttcagga ccaggattta ctggtgggga cttagttaga    1500
ttaaatagta gtggaaataa cattcagaat agagggtata ttgaagttcc aattcacttc    1560
ccatcgacat ctaccagata tcgagttcgt gtacggtatg cttctgtaac cccgattcac    1620
ctcaacgtta attggggtaa ttcatccatt ttttccaata cagtaccagc tacagctacg    1680
tcattagata atctacaatc aagtgatttt ggttattttg aaagtgccaa tgcttttaca    1740
tcttcattag gtaatatagt aggtgttaga aattttagtg ggactgcagg agtgataata    1800
gacagatttg aatttattcc agttactgca acactcgagc cggagaggat tactcaaata    1860
ccattggtaa aagcacatac acttcagtca ggtactactg ttgtaagagg gcccgggttt    1920 acggaggag atattcttcg acgaacaagt ggaggaccat ttgcttatac tattgttaat     1980
ataaatgggc aattacccca aaggtatcgt gcaagaatac gctatgcctc tactacaaat    2040
ctaagaattt acgtaacggt tgcaggtgaa cggattttg ctggtcaatt aacaaaaca     2100 atggataccg gtgacccatt aacattccaa tcttttagtt acgcaactat taatacagct   2160
tttacattcc caatgagcca gagtagtttc acagtaggtg ctgatacttt tagttcaggg   2220
aatgaagttt atatagacag atttgaattg attccagtta ctctcgaggc tgaatataat   2280
ctggaaagag cgcagaaggc ggtgaatgcg ctgtttacgt ctacaaacca actagggcta   2340
aaaacaaatg taacggatta tcatattgat caagtgtcca atttagttac gtatttatcg   2400
gatgaatttt gtctggatga aaagcgagaa ttgtccgaga agtcaaaaca tgcgaagcga   2460
ctcagtgatg aacgcaattt actccaagat tcaaatttca aagacattaa taggcaacca   2520
gaacgtgggt ggggcggaag tacagggatt accatccaag gagggatga cgtatttaaa    2580 gaaaattacg tcacactatc aggtaccttt gatgagtgct atccaacata tttgtatcaa   2640
aaaatcgatg aatcaaaatt aaaagccttt acccgttatc aattaagagg gtatatcgaa   2700
gatagtcaag acttagaaat ctatttaatt cgctacaatg caaaacatga aacagtaaat   2760
gtgccaggta cgggttcctt atggccgctt tcagcccaaa gtccaatcgg aaagtgtgga   2820
gagccgaatc gatgcgcgcc acaccttgaa tggaatcctg acttagattg ttcgtgtagg   2880
gatggagaaa agtgtgccca tcattcgcat catttctcct tagacattga tgtaggatgt   2940
acagacttaa atgaggacct aggtgtatgg gtgatcttta agattaagac gcaagatggg   3000
cacgcaagac tagggaatct agagtttctc gaagagaaac cattagtagg agaagcgcta   3060
gctcgtgtga aaagagcgga gaaaaatgg agagacaaac gtgaaaaatt ggaatgggaa     3120
acaaatatcg tttataaaga ggcaaaagaa tctgtagatg ctttatttgt aaactctcaa   3180
tatgatcaat tacaagcgga tacgaatatt gccatgattc atgcggcaga taaacgtgtt   3240
catagcattc gagaagctta tctgcctgag ctgtctgtga ttccgggtgt caatgcggct   3300 attttttgaag aattagaagg gcgtattttc actgcattct ccctatatga tgcgagaaat   3360
gtcattaaaa atggtgattt taataatggc ttatcctgct ggaacgtgaa agggcatgta   3420
gatgtagaag aacaaaacaa ccaacgttcg gtccttgttg ttccggaatg ggaagcagaa   3480
gtgtcacaag aagttcgtgt ctgtccgggt cgtggctata tccttcgtgt cacagcgtac   3540
aaggagggat atggagaagg ttgcgtaacc attcatgaga tcgagaacaa tacagacgaa   3600
ctgaagttta gcaactgcgt agaagaggaa atctatccaa ataacacggt aacgtgtaat   3660
gattatactg taaatcaaga agaatacgga ggtgcgtaca cttctcgtaa tcgaggatat   3720
aacgaagctc cttccgtacc agctgattat gcgtcagtct atgaagaaaa atcgtataca   3780
gatggacgaa gagagaatcc ttgtgaattt aacagagggt atagggatta cacgccacta   3840
```

```
ccagttggtt atgtgacaaa agaattagaa tacttcccag aaaccgataa ggtatggatt    3900
gagattggag aaacggaagg aacatttatc gtggacagcg tggaattact ccttatggag    3960
gaa                                                                  3963
```

<210> SEQ ID NO 3
<211> LENGTH: 1341
<212> TYPE: PRT
<213> ORGANISM: Artificial sequence
<220> FEATURE:
<223> OTHER INFORMATION: Synthetic

<400> SEQUENCE: 3

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335
```

-continued

```
Leu Tyr Gly Thr Met Gly Asn Ala Ala Pro Gln Gln Arg Ile Val Ala
                340                 345                 350
Gln Leu Gly Gln Gly Val Tyr Arg Thr Leu Ser Ser Thr Leu Tyr Arg
            355                 360                 365
Arg Pro Phe Asn Ile Gly Ile Asn Asn Gln Gln Leu Ser Val Leu Asp
370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
            420                 425                 430
Val Ser Met Phe Arg Ser Gly Phe Ser Asn Ser Ser Val Ser Ile Ile
        435                 440                 445
Arg Ala Pro Met Phe Ser Trp Ile His Arg Ser Ala Glu Val Asn Asn
    450                 455                 460
Ile Ile Ala Ser Asp Ser Ile Thr Gln Ile Pro Ala Val Lys Gly Asn
465                 470                 475                 480
Phe Leu Phe Asn Gly Ser Val Ile Ser Gly Pro Gly Phe Thr Gly Gly
                485                 490                 495
Asp Leu Val Arg Leu Asn Ser Ser Gly Asn Asn Ile Gln Asn Arg Gly
            500                 505                 510
Tyr Ile Glu Val Pro Ile His Phe Pro Ser Thr Ser Thr Arg Tyr Arg
        515                 520                 525
Val Arg Val Arg Tyr Ala Ser Val Thr Pro Ile His Leu Asn Val Asn
    530                 535                 540
Trp Gly Asn Ser Ser Ile Phe Ser Asn Thr Val Pro Ala Thr Ala Thr
545                 550                 555                 560
Ser Leu Asp Asn Leu Gln Ser Ser Asp Phe Gly Tyr Phe Glu Ser Ala
                565                 570                 575
Asn Ala Phe Thr Ser Ser Leu Gly Asn Ile Val Gly Val Arg Asn Phe
            580                 585                 590
Ser Gly Thr Ala Gly Val Ile Ile Asp Arg Phe Glu Phe Ile Pro Val
        595                 600                 605
Thr Ala Thr Leu Glu Asn Ile His Ala Val His Glu Asn Gly Ser Met
    610                 615                 620
Ile His Leu Ala Pro Asn Asp Tyr Thr Gly Phe Thr Ile Ser Pro Ile
625                 630                 635                 640
His Ala Thr Gln Val Asn Asn Gln Thr Arg Thr Phe Ile Ser Glu Lys
                645                 650                 655
Phe Gly Asn Gln Gly Asp Ser Leu Arg Phe Glu Gln Asn Asn Thr Thr
            660                 665                 670
Ala Arg Tyr Thr Leu Arg Gly Asn Gly Asn Ser Tyr Asn Leu Tyr Leu
        675                 680                 685
Arg Val Ser Ser Ile Gly Asn Ser Thr Ile Arg Val Thr Ile Asn Gly
    690                 695                 700
Arg Val Tyr Thr Ala Thr Asn Val Asn Thr Thr Thr Asn Asn Asp Gly
705                 710                 715                 720
Val Asn Asp Asn Gly Ala Arg Phe Ser Asp Ile Asn Ile Gly Asn Val
                725                 730                 735
Val Ala Ser Ser Asn Ser Asp Val Pro Leu Asp Ile Asn Val Thr Leu
            740                 745                 750
Asn Ser Gly Thr Gln Phe Asp Leu Met Asn Ile Met Leu Val Pro Thr
        755                 760                 765
```

```
Asn Ile Ser Pro Leu Tyr Leu Glu Ala Glu Tyr Asn Leu Glu Arg Ala
    770             775                 780

Gln Lys Ala Val Asn Ala Leu Phe Thr Ser Thr Asn Gln Leu Gly Leu
785             790                 795                 800

Lys Thr Asn Val Thr Asp Tyr His Ile Asp Gln Val Ser Asn Leu Val
                805                 810                 815

Thr Tyr Leu Ser Asp Glu Phe Cys Leu Asp Glu Lys Arg Glu Leu Ser
            820                 825                 830

Glu Lys Val Lys His Ala Lys Arg Leu Ser Asp Glu Arg Asn Leu Leu
                835                 840                 845

Gln Asp Ser Asn Phe Lys Asp Ile Asn Arg Gln Pro Glu Arg Gly Trp
            850                 855                 860

Gly Gly Ser Thr Gly Ile Thr Ile Gln Gly Gly Asp Asp Val Phe Lys
865                 870                 875                 880

Glu Asn Tyr Val Thr Leu Ser Gly Thr Phe Asp Glu Cys Tyr Pro Thr
                885                 890                 895

Tyr Leu Tyr Gln Lys Ile Asp Glu Ser Lys Leu Lys Ala Phe Thr Arg
            900                 905                 910

Tyr Gln Leu Arg Gly Tyr Ile Glu Asp Ser Gln Asp Leu Glu Ile Tyr
                915                 920                 925

Leu Ile Arg Tyr Asn Ala Lys His Glu Thr Val Asn Val Pro Gly Thr
            930                 935                 940

Gly Ser Leu Trp Pro Leu Ser Ala Gln Ser Pro Ile Gly Lys Cys Gly
945                 950                 955                 960

Glu Pro Asn Arg Cys Ala Pro His Leu Glu Trp Asn Pro Asp Leu Asp
                965                 970                 975

Cys Ser Cys Arg Asp Gly Glu Lys Cys Ala His His Ser His His Phe
            980                 985                 990

Ser Leu Asp Ile Asp Val Gly Cys Thr Asp Leu Asn Glu Asp Leu Gly
            995                 1000                1005

Val Trp Val Ile Phe Lys Ile Lys Thr Gln Asp Gly His Ala Arg Leu
    1010            1015                1020

Gly Asn Leu Glu Phe Leu Glu Glu Lys Pro Leu Val Gly Glu Ala Leu
1025            1030                1035                1040

Ala Arg Val Lys Arg Ala Glu Lys Lys Trp Arg Asp Lys Arg Glu Lys
                1045                1050                1055

Leu Glu Trp Glu Thr Asn Ile Val Tyr Lys Glu Ala Lys Glu Ser Val
            1060                1065                1070

Asp Ala Leu Phe Val Asn Ser Gln Tyr Asp Gln Leu Gln Ala Asp Thr
            1075                1080                1085

Asn Ile Ala Met Ile His Ala Ala Asp Lys Arg Val His Ser Ile Arg
            1090                1095                1100

Glu Ala Tyr Leu Pro Glu Leu Ser Val Ile Pro Gly Val Asn Ala Ala
1105            1110                1115                1120

Ile Phe Glu Glu Leu Glu Gly Arg Ile Phe Thr Ala Phe Ser Leu Tyr
                1125                1130                1135

Asp Ala Arg Asn Val Ile Lys Asn Gly Asp Phe Asn Asn Gly Leu Ser
            1140                1145                1150

Cys Trp Asn Val Lys Gly His Val Asp Val Glu Glu Gln Asn Asn Gln
            1155                1160                1165

Arg Ser Val Leu Val Val Pro Glu Trp Glu Ala Glu Val Ser Gln Glu
    1170                1175                1180

Val Arg Val Cys Pro Gly Arg Gly Tyr Ile Leu Arg Val Thr Ala Tyr
```

|  |  | 1185 |  |  | 1190 |  |  | 1195 |  |  | 1200 |  |
|---|---|---|---|---|---|---|---|---|---|---|---|---|
| Lys | Glu | Gly | Tyr | Gly | Glu | Gly | Cys | Val | Thr | Ile | His | Glu | Ile | Glu | Asn |
|  |  |  |  | 1205 |  |  |  |  | 1210 |  |  |  |  | 1215 |  |

| Asn | Thr | Asp | Glu | Leu | Lys | Phe | Ser | Asn | Cys | Val | Glu | Glu | Glu | Ile | Tyr |
|  |  |  | 1220 |  |  |  |  | 1225 |  |  |  |  | 1230 |  |  |

| Pro | Asn | Asn | Thr | Val | Thr | Cys | Asn | Asp | Tyr | Thr | Val | Asn | Gln | Glu | Glu |
|  |  |  | 1235 |  |  |  |  | 1240 |  |  |  |  | 1245 |  |  |

| Tyr | Gly | Gly | Ala | Tyr | Thr | Ser | Arg | Asn | Arg | Gly | Tyr | Asn | Glu | Ala | Pro |
|  |  | 1250 |  |  |  |  | 1255 |  |  |  |  | 1260 |  |  |  |

| Ser | Val | Pro | Ala | Asp | Tyr | Ala | Ser | Val | Tyr | Glu | Glu | Lys | Ser | Tyr | Thr |
| 1265 |  |  |  |  | 1270 |  |  |  |  | 1275 |  |  |  |  | 1280 |

| Asp | Gly | Arg | Arg | Glu | Asn | Pro | Cys | Glu | Phe | Asn | Arg | Gly | Tyr | Arg | Asp |
|  |  |  |  | 1285 |  |  |  |  | 1290 |  |  |  |  | 1295 |  |

| Tyr | Thr | Pro | Leu | Pro | Val | Gly | Tyr | Val | Thr | Lys | Glu | Leu | Glu | Tyr | Phe |
|  |  |  | 1300 |  |  |  |  | 1305 |  |  |  |  | 1310 |  |  |

| Pro | Glu | Thr | Asp | Lys | Val | Trp | Ile | Glu | Ile | Gly | Glu | Thr | Glu | Gly | Thr |
|  |  | 1315 |  |  |  |  | 1320 |  |  |  |  | 1325 |  |  |  |

| Phe | Ile | Val | Asp | Ser | Val | Glu | Leu | Leu | Leu | Met | Glu | Glu |
|  |  | 1330 |  |  |  |  | 1335 |  |  |  | 1340 |  |

<210> SEQ ID NO 4
<211> LENGTH: 4023
<212> TYPE: DNA
<213> ORGANISM: Artificial sequence
<220> FEATURE:
<223> OTHER INFORMATION: Synthetic

<400> SEQUENCE: 4

```
atggataaca atccgaacat caatgaatgc attccttata attgtttaag taaccctgaa      60
gtagaagtat taggtggaga agaatagaa actggttaca ccccaatcga tatttccttg     120
tcgctaacgc aatttctttt gagtgaattt gttcccggtg ctggatttgt gttaggacta     180
gttgatataa tatggggaat ttttggtccc tctcaatggg acgcatttct tgtacaaatt     240
gaacagttaa ttaaccaaag aatagaagaa ttcgctagga accaagccat ttctagatta     300
gaaggactaa gcaatcttta tcaaatttac gcagaatctt ttagagagtg ggaagcagat     360
cctactaatc cagcattaag agaagagatg cgtattcaat tcaatgacat gaacagtgcc     420
cttacaaccg ctattcctct tttggcagtt caaaattatc aagttcctct tttatcagta     480
tatgttcaag ctgcaaattt acatttatca gttttgagag atgttcagt gtttggacaa     540
aggtggggat tgatgccgc gactatcaat agtcgttata atgatttaac taggcttatt     600
ggcaactata cagattatgc tgtacgctgg tacaatacgg gattagaacg tgtatgggga     660
ccggattcta gagattgggt aaggtataat caatttagaa gagaattaac actaactgta     720
ttagatatcg ttgctctgtt cccgaattat gatagtagaa gatatccaat tcgtacggtt     780
tcccaattaa caagagaaat ttatacaaac ccagtattag aaaattttga tggtagtttt     840
cgaggctcgg ctcagggcat agaaagaagt attaggagtc cacatttgat ggatatactt     900
aacagtataa ccatctatac ggatgctcat agggttatt attattggtc agggcatcaa     960
ataatggctt ctcctgtcgg ttttcgggg ccagaattca cgtttccgct atatggaacc    1020
atgggaaatg cagctccaca caacgtatt gttgctcaac taggtcaggg cgtgtataga    1080
acattatcgt ccactttata tagaagacct tttaatatag gataaataa tcaacaacta    1140
tctgttcttg acgggacaga atttgctat ggaacctcct caaatttgcc atccgctgta    1200
tacagaaaaa gcggaacggt agattcgctg gatgaaatac cgccacagaa taacaacgtg    1260
```

```
ccacctaggc aaggatttag tcatcgatta agccatgttt caatgtttcg ttcaggcttt    1320
agtaatagta gtgtaagtat aataagagct cctatgttct cttggataca tcgtagtgct    1380
gaagttaaca atataattgc atcggatagt attactcaaa tccctgcagt gaagggaaac    1440
tttcttttta atggttctgt aatttcagga ccaggattta ctggtgggga cttagttaga    1500
ttaaatagta gtggaaataa cattcagaat agagggtata ttgaagttcc aattcacttc    1560
ccatcgacat ctaccagata tcgagttcgt gtacggtatg cttctgtaac cccgattcac    1620
ctcaacgtta attggggtaa ttcatccatt ttttccaata cagtaccagc tacagctacg    1680
tcattagata atctacaatc aagtgatttt ggttattttg aaagtgccaa tgcttttaca    1740
tcttcattag gtaatatagt aggtgttaga aattttagtg ggactgcagg agtgataata    1800
gacagatttg aatttattcc agttactgca acactcgaga atatccatgc tgttcatgaa    1860
aatggttcta tgattcattt agcgccaaat gactatacag gatttactat ttcgccgata    1920
catgcaactc aagtgaataa tcaaacacga acatttattt ctgaaaaatt tggaaatcaa    1980
ggtgattctt aaggtttga acaaaacaac acgacagctc gttatacgct tagagggaat    2040
ggaaatagtt acaatcttta tttaagagtt tcttcaatag gaaattccac tattcgagtt    2100
actataaacg gtagggtata tactgctaca aatgttaata ctactacaaa taacgatgga    2160
gttaatgata atggagctcg ttttcagat attaatatcg gtaatgtagt agcaagtagt    2220
aattctgatg taccattaga tataaatgta acattaaact ccggtactca atttgatctt    2280
atgaatatta tgcttgtacc aactaatatt tcaccacttt atctcgaggc tgaatataat    2340
ctggaaagag cgcagaaggc ggtgaatgcg ctgtttacgt ctacaaacca actagggcta    2400
aaaacaaatg taacggatta tcatattgat caagtgtcca atttagttac gtatttatcg    2460
gatgaatttt gtctggatga aaagcgagaa ttgtccgaga aagtcaaaca tgcgaagcga    2520
ctcagtgatg aacgcaattt actccaagat tcaaatttca aagacattaa taggcaacca    2580
gaacgtgggt ggggcggaag tacagggatt accatccaag gagggatga cgtatttaaa    2640 gaaaattacg tcacactatc aggtacctt gatgagtgct atccaacata tttgtatcaa    2700
aaaatcgatg aatcaaaatt aaaagccttt acccgttatc aattaagagg gtatatcgaa    2760
gatagtcaag acttagaaat ctatttaatt cgctacaatg caaaacatga aacagtaaat    2820
gtgccaggta cgggttcctt atggccgctt tcagcccaaa gtccaatcgg aaagtgtgga    2880
gagccgaatc gatgcgcgcc acaccttgaa tggaatcctg acttagattg ttcgtgtagg    2940
gatggagaaa agtgtgccca tcattcgcat catttctcct tagacattga tgtaggatgt    3000
acagacttaa atgaggacct aggtgtatgg gtgatcttta agattaagac gcaagatggg    3060
cacgcaagac tagggaatct agagtttctc gaagagaaac cattagtagg agaagcgcta    3120
gctcgtgtga aaagagcgga gaaaaaatgg agagacaaac gtgaaaaatt ggaatgggaa    3180
acaaatatcg tttataaaga ggcaaaagaa tctgtagatg ctttatttgt aaactctcaa    3240
tatgatcaat acaagcggaa tacgaatatt gccatgattc atgcggcaga taaacgtgtt    3300
catagcattc gagaagctta tctgcctgag ctgtctgtga ttccgggtgt caatgcggct    3360 attttttgaag aattagaagg gcgtattttc actgcattct ccctatatga tgcgagaaat    3420
gtcattaaaa atggtgattt taataatggc ttatcctgct ggaacgtgaa agggcatgta    3480
gatgtagaag aacaaaacaa ccaacgttcg gtccttgttg ttccggaatg ggaagcagaa    3540
gtgtcacaag aagttcgtgt ctgtccgggt cgtggctata tccttcgtgt cacagcgtac    3600
aaggagggat atggagaagg ttgcgtaacc attcatgaga tcgagaacaa tacagacgaa    3660
```

```
ctgaagttta gcaactgcgt agaagaggaa atctatccaa ataacacggt aacgtgtaat    3720
gattatactg taaatcaaga agaatacgga ggtgcgtaca cttctcgtaa tcgaggatat    3780
aacgaagctc cttccgtacc agctgattat gcgtcagtct atgaagaaaa atcgtataca    3840
gatggacgaa gagagaatcc ttgtgaattt aacagagggt atagggatta cacgccacta    3900
ccagttggtt atgtgacaaa agaattagaa tacttcccag aaaccgataa ggtatggatt    3960
gagattggag aaacggaagg aacatttatc gtggacagcg tggaattact ccttatggag    4020
gaa                                                                  4023
```

<210> SEQ ID NO 5
<211> LENGTH: 1323
<212> TYPE: PRT
<213> ORGANISM: Artificial sequence
<220> FEATURE:
<223> OTHER INFORMATION: Synthetic

<400> SEQUENCE: 5

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
```

```
            290                 295                 300
Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
                355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Val Ser Ile Ile
                435                 440                 445

Arg Ala Pro Met Phe Ser Trp Ile His Arg Ser Ala Glu Val Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
                500                 505                 510

Tyr Ile Glu Val Pro Ile His Phe Pro Ser Thr Ser Thr Arg Tyr Arg
                515                 520                 525

Val Arg Val Arg Tyr Ala Ser Val Thr Pro Ile His Leu Asn Val Asn
                530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Ser Leu Gly Asn Ile Val Gly Val Arg Asn Phe
                580                 585                 590

Ser Gly Thr Ala Gly Val Ile Ile Asp Arg Phe Glu Phe Ile Pro Val
                595                 600                 605

Thr Ala Thr Leu Glu Ala Glu Lys Ile Thr Gln Leu Pro Val Val Lys
610                 615                 620

Ala Tyr Ala Leu Ser Ser Gly Ala Ser Ile Ile Glu Gly Pro Gly Phe
625                 630                 635                 640

Thr Gly Gly Asn Leu Leu Phe Leu Lys Glu Ser Ser Asn Ser Ile Ala
                645                 650                 655

Lys Phe Lys Val Thr Leu Asn Ser Ala Ala Leu Leu Gln Arg Tyr Arg
                660                 665                 670

Val Arg Ile Arg Tyr Ala Ser Thr Thr Asn Leu Arg Leu Phe Val Gln
                675                 680                 685

Asn Ser Asn Asn Asp Phe Leu Val Ile Tyr Ile Asn Lys Thr Met Asn
                690                 695                 700

Lys Asp Asp Asp Leu Thr Tyr Gln Thr Phe Asp Leu Ala Thr Thr Asn
705                 710                 715                 720
```

-continued

```
Ser Asn Met Gly Phe Ser Gly Asp Lys Asn Glu Leu Ile Ile Gly Ala
            725                 730                 735
Glu Ser Phe Val Ser Asn Glu Lys Ile Tyr Ile Asp Lys Ile Glu Phe
        740                 745                 750
Ile Pro Val Gln Leu Glu Ala Glu Tyr Asn Leu Glu Arg Ala Gln Lys
    755                 760                 765
Ala Val Asn Ala Leu Phe Thr Ser Thr Asn Gln Leu Gly Leu Lys Thr
770                 775                 780
Asn Val Thr Asp Tyr His Ile Asp Gln Val Ser Asn Leu Val Thr Tyr
785                 790                 795                 800
Leu Ser Asp Glu Phe Cys Leu Asp Glu Lys Arg Glu Leu Ser Glu Lys
                805                 810                 815
Val Lys His Ala Lys Arg Leu Ser Asp Glu Arg Asn Leu Leu Gln Asp
            820                 825                 830
Ser Asn Phe Lys Asp Ile Asn Arg Gln Pro Glu Arg Gly Trp Gly Gly
        835                 840                 845
Ser Thr Gly Ile Thr Ile Gln Gly Gly Asp Asp Val Phe Lys Glu Asn
    850                 855                 860
Tyr Val Thr Leu Ser Gly Thr Phe Asp Glu Cys Tyr Pro Thr Tyr Leu
865                 870                 875                 880
Tyr Gln Lys Ile Asp Glu Ser Lys Leu Lys Ala Phe Thr Arg Tyr Gln
                885                 890                 895
Leu Arg Gly Tyr Ile Glu Asp Ser Gln Asp Leu Glu Ile Tyr Leu Ile
            900                 905                 910
Arg Tyr Asn Ala Lys His Glu Thr Val Asn Val Pro Gly Thr Gly Ser
        915                 920                 925
Leu Trp Pro Leu Ser Ala Gln Ser Pro Ile Gly Lys Cys Gly Glu Pro
    930                 935                 940
Asn Arg Cys Ala Pro His Leu Glu Trp Asn Pro Asp Leu Asp Cys Ser
945                 950                 955                 960
Cys Arg Asp Gly Glu Lys Cys Ala His His Ser His His Phe Ser Leu
                965                 970                 975
Asp Ile Asp Val Gly Cys Thr Asp Leu Asn Glu Asp Leu Gly Val Trp
            980                 985                 990
Val Ile Phe Lys Ile Lys Thr Gln Asp Gly His Ala Arg Leu Gly Asn
        995                 1000                1005
Leu Glu Phe Leu Glu Glu Lys Pro Leu Val Gly Glu Ala Leu Ala Arg
    1010                1015                1020
Val Lys Arg Ala Glu Lys Lys Trp Arg Asp Lys Arg Glu Lys Leu Glu
1025                1030                1035                1040
Trp Glu Thr Asn Ile Val Tyr Lys Glu Ala Lys Glu Ser Val Asp Ala
                1045                1050                1055
Leu Phe Val Asn Ser Gln Tyr Asp Gln Leu Gln Ala Asp Thr Asn Ile
            1060                1065                1070
Ala Met Ile His Ala Ala Asp Lys Arg Val His Ser Ile Arg Glu Ala
        1075                1080                1085
Tyr Leu Pro Glu Leu Ser Val Ile Pro Gly Val Asn Ala Ala Ile Phe
    1090                1095                1100
Glu Glu Leu Glu Gly Arg Ile Phe Thr Ala Phe Ser Leu Tyr Asp Ala
1105                1110                1115                1120
Arg Asn Val Ile Lys Asn Gly Asp Phe Asn Asn Gly Leu Ser Cys Trp
                1125                1130                1135
Asn Val Lys Gly His Val Asp Val Glu Glu Gln Asn Asn Gln Arg Ser
            1140                1145                1150
```

Val Leu Val Val Pro Glu Trp Glu Ala Glu Val Ser Gln Glu Val Arg
        1155                1160                1165

Val Cys Pro Gly Arg Gly Tyr Ile Leu Arg Val Thr Ala Tyr Lys Glu
    1170                1175                1180

Gly Tyr Gly Glu Gly Cys Val Thr Ile His Glu Ile Glu Asn Asn Thr
1185                1190                1195                1200

Asp Glu Leu Lys Phe Ser Asn Cys Val Glu Glu Ile Tyr Pro Asn
            1205                1210                1215

Asn Thr Val Thr Cys Asn Asp Tyr Thr Val Asn Gln Glu Glu Tyr Gly
            1220                1225                1230

Gly Ala Tyr Thr Ser Arg Asn Arg Gly Tyr Asn Glu Ala Pro Ser Val
        1235                1240                1245

Pro Ala Asp Tyr Ala Ser Val Tyr Glu Glu Lys Ser Tyr Thr Asp Gly
        1250                1255                1260

Arg Arg Glu Asn Pro Cys Glu Phe Asn Arg Gly Tyr Arg Asp Tyr Thr
1265                1270                1275                1280

Pro Leu Pro Val Gly Tyr Val Thr Lys Glu Leu Glu Tyr Phe Pro Glu
            1285                1290                1295

Thr Asp Lys Val Trp Ile Glu Ile Gly Glu Thr Glu Gly Thr Phe Ile
            1300                1305                1310

Val Asp Ser Val Glu Leu Leu Leu Met Glu Glu
        1315                1320

<210> SEQ ID NO 6
<211> LENGTH: 3969
<212> TYPE: DNA
<213> ORGANISM: Artificial sequence
<220> FEATURE:
<223> OTHER INFORMATION: Synthetic

<400> SEQUENCE: 6

```
atggataaca atccgaacat caatgaatgc attccttata attgtttaag taaccctgaa      60
gtagaagtat taggtggaga aagaatagaa actggttaca ccccaatcga tatttccttg     120
tcgctaacgc aatttctttt gagtgaattt gttcccggtg ctggatttgt gttaggacta     180
gttgatataa tatggggaat ttttggtccc tctcaatggg acgcatttct tgtacaaatt     240
gaacagttaa ttaaccaaag aatagaagaa ttcgctagga accaagccat ttctagatta     300
gaaggactaa gcaatcttta tcaaatttac gcagaatctt ttagagagtg ggaagcagat     360
cctactaatc cagcattaag agaagagatg cgtattcaat tcaatgacat gaacagtgcc     420
cttacaaccg ctattcctct tttggcagtt caaaattatc aagttcctct tttatcagta     480
tatgttcaag ctgcaaattt acatttatca gttttgagag atgtttcagt gtttggacaa     540
aggtggggat tgatgccgc gactatcaat agtcgttata atgatttaac taggcttatt     600
ggcaactata cagattatgc tgtacgctgg tacaatacgg gattagaacg tgtatgggga     660
ccggattcta gagattgggt aaggtataat caatttagaa gagaattaac actaactgta     720
ttagatatcg ttgctctgtt cccgaattat gatagtagaa gatatccaat tcgtacggtt     780
tcccaattaa caagagaaat ttatacaaac ccagtattag aaaattttga tggtagtttt     840
cgaggctcgg ctcagggcat agaaagaagt attaggagtc cacatttgat ggatatactt     900
aacagtataa ccatctatac ggatgctcat aggggttatt attattggtc agggcatcaa     960
ataatggctt ctcctgtcgg ttttcggggg ccagaattca cgtttccgct atatggaacc    1020
atgggaaatg cagctccaca acaacgtatt gttgctcaac taggtcaggg cgtgtataga    1080
```

```
acattatcgt ccactttata tagaagacct tttaatatag ggataaataa tcaacaacta    1140
tctgttcttg acgggacaga atttgcttat ggaacctcct caaatttgcc atccgctgta    1200
tacagaaaaa gcggaacggt agattcgctg gatgaaatac cgccacagaa taacaacgtg    1260
ccacctaggc aaggatttag tcatcgatta agccatgttt caatgtttcg ttcaggcttt    1320
agtaatagta gtgtaagtat aataagagct cctatgttct cttggataca tcgtagtgct    1380
gaagttaaca atataattgc atcggatagt attactcaaa tccctgcagt gaagggaaac    1440
tttcttttta atggttctgt aatttcagga ccaggattta ctggtgggga cttagttaga    1500
ttaaatagta gtggaaataa cattcagaat agagggtata ttgaagttcc aattcacttc    1560
ccatcgacat ctaccagata tcgagttcgt gtacggtatg cttctgtaac cccgattcac    1620
ctcaacgtta attggggtaa ttcatccatt ttttccaata cagtaccagc tacagctacg    1680
tcattagata atctacaatc aagtgatttt ggttattttg aaagtgccaa tgctttttaca   1740 tcttcattag gtaatatagt aggtgttaga aattttagtg ggactgcagg agtgataata    1800
gacagatttg aatttattcc agttactgca acactcgagg ctgaaaagat tactcaactt    1860
ccagtagtga aagcatatgc cttgtcttca ggtgcttcca ttattgaagg tccaggattc    1920
acaggaggaa atttactatt cctaaaagaa tctagtaatt caattgctaa atttaaagtt    1980
acattaaatt cagcagcctt gttacaacga tatcgtgtaa aatacgcta tgcttctacc     2040 actaacttac gacttttgt gcaaaattca aacaatgatt ttcttgtcat ctacattaat     2100
aaaactatga ataaagatga tgatttaaca tatcaaacat ttgatctcgc aactactaat    2160
tctaatatgg ggttctcggg tgataagaat gaacttataa taggagcaga atctttcgtt    2220
tctaatgaaa aaatctatat agataagata gaatttatcc cagtacaact cgaggctgaa    2280
tataatctgg aaagagcgca gaaggcggtg aatgcgctgt ttacgtctac aaaccaacta    2340
gggctaaaaa caaatgtaac ggattatcat attgatcaag tgtccaattt agttacgtat    2400
ttatcggatg aattttgtct ggatgaaaag cgagaattgt ccgagaaagt caaacatgcg    2460
aagcgactca gtgatgaacg caatttactc caagattcaa atttcaaaga cattaatagg    2520
caaccagaac gtgggtgggg cggaagtaca gggattacca tccaaggagg ggatgacgta    2580 tttaagaaa attacgtcac actatcaggt accttgatg agtgctatcc aacatatttg       2640
tatcaaaaaa tcgatgaatc aaaattaaaa gcctttaccc gttatcaatt aagagggtat    2700
atcgaagata gtcaagactt agaaatctat ttaattcgct acaatgcaaa acatgaaaca    2760
gtaaatgtgc caggtacggg ttccttatgg ccgctttcag cccaaagtcc aatcggaaag    2820
tgtggagagc cgaatcgatg cgcgccacac cttgaatgga atcctgactt agattgttcg    2880
tgtagggatg gagaaaagtg tgcccatcat tcgcatcatt tctccttaga cattgatgta    2940
ggatgtacag acttaaatga ggacctaggt gtatgggtga tctttaagat taagacgcaa    3000
gatgggcacg caagactagg gaatctagag tttctcgaag agaaaccatt agtaggagaa    3060
gcgctagctc gtgtgaaaag agcggagaaa aaatggagag acaaacgtga aaaattggaa    3120
tgggaaacaa atatcgttta taagaggca aaagaatctg tagatgcttt atttgtaaac     3180
tctcaatatg atcaattaca agcggatacg aatattgcca tgattcatgc ggcagataaa    3240
cgtgttcata gcattcgaga agcttatctg cctgagctgt ctgtgattcc gggtgtcaat    3300
gcggctattt ttgaagaatt agaagggcgt attttcactg cattctccct atatgatgcg    3360
agaaatgtca ttaaaaatgg tgattttaat aatggcttat cctgctggaa cgtgaaaggg    3420
catgtagatg tagaagaaca aaacaaccaa cgttcggtcc ttgttgttcc ggaatgggaa    3480
```

-continued

```
gcagaagtgt cacaagaagt tcgtgtctgt ccgggtcgtg gctatatcct tcgtgtcaca    3540
gcgtacaagg agggatatgg agaaggttgc gtaaccattc atgagatcga gaacaataca    3600
gacgaactga agtttagcaa ctgcgtagaa gaggaaatct atccaaataa cacggtaacg    3660
tgtaatgatt atactgtaaa tcaagaagaa tacggaggtg cgtacacttc tcgtaatcga    3720
ggatataacg aagctccttc cgtaccagct gattatgcgt cagtctatga gaaaaatcg     3780 tatacagatg gacgaagaga gaatccttgt gaatttaaca gagggtatag ggattacacg    3840
ccactaccag ttggttatgt gacaaaagaa ttagaatact tcccagaaac cgataaggta    3900
tggattgaga ttggagaaac ggaaggaaca tttatcgtgg acagcgtgga attactcctt    3960
atggaggaa                                                            3969
```

<210> SEQ ID NO 7
<211> LENGTH: 1178
<212> TYPE: PRT
<213> ORGANISM: Bacillus thuringiensis

<400> SEQUENCE: 7

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285
```

-continued

Gly Ser Ile Arg Ser Pro His Leu Met Asp Ile Leu Asn Ser Ile Thr
290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
            325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
            405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
            485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
            565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu Glu Arg Ala Gln Lys Ala
610                 615                 620

Val Asn Ala Leu Phe Thr Ser Thr Asn Gln Leu Gly Leu Lys Thr Asn
625                 630                 635                 640

Val Thr Asp Tyr His Ile Asp Gln Val Ser Asn Leu Val Thr Tyr Leu
            645                 650                 655

Ser Asp Glu Phe Cys Leu Asp Glu Lys Arg Glu Leu Ser Glu Lys Val
            660                 665                 670

Lys His Ala Lys Arg Leu Ser Asp Glu Arg Asn Leu Leu Gln Asp Ser
            675                 680                 685

Asn Phe Lys Asp Ile Asn Arg Gln Pro Glu Arg Gly Trp Gly Gly Ser
690                 695                 700

Thr Gly Ile Thr Ile Gln Gly Gly Asp Asp Val Phe Lys Glu Asn Tyr
705                 710                 715                 720

-continued

```
Val Thr Leu Ser Gly Thr Phe Asp Glu Cys Tyr Pro Thr Tyr Leu Tyr
            725                 730                 735

Gln Lys Ile Asp Glu Ser Lys Leu Lys Ala Phe Thr Arg Tyr Gln Leu
            740                 745                 750

Arg Gly Tyr Ile Glu Asp Ser Gln Asp Leu Glu Ile Tyr Ser Ile Arg
            755                 760                 765

Tyr Asn Ala Lys His Glu Thr Val Asn Val Pro Gly Thr Gly Ser Leu
            770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
                805                 810                 815

Arg Asp Gly Glu Lys Cys Ala His His Ser His Phe Ser Leu Asp
            820                 825                 830

Ile Asp Val Gly Cys Thr Asp Leu Asn Glu Asp Leu Gly Val Trp Val
            835                 840                 845

Ile Phe Lys Ile Lys Thr Gln Asp Gly His Ala Arg Leu Gly Asn Leu
            850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
                885                 890                 895

Glu Thr Asn Ile Val Tyr Lys Glu Ala Lys Glu Ser Val Asp Ala Leu
            900                 905                 910

Phe Val Asn Ser Gln Tyr Asp Gln Leu Gln Ala Asp Thr Asn Ile Ala
            915                 920                 925

Met Ile His Ala Ala Asp Lys Arg Val His Ser Ile Arg Glu Ala Tyr
            930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
            980                 985                 990

Val Lys Gly His Val Asp Val Glu Glu Gln Asn Asn Gln Arg Ser Val
            995                1000                1005

Leu Val Val Pro Glu Trp Glu Ala Glu Val Ser Gln Glu Val Arg Val
            1010                1015                1020

Cys Pro Gly Arg Gly Tyr Ile Leu Arg Val Thr Ala Tyr Lys Glu Gly
1025                1030                1035                1040

Tyr Gly Glu Gly Cys Val Thr Ile His Glu Ile Glu Asn Asn Thr Asp
                1045                1050                1055

Glu Leu Lys Phe Ser Asn Cys Val Glu Glu Ile Tyr Pro Asn Asn
            1060                1065                1070

Thr Val Thr Cys Asn Asp Tyr Thr Val Asn Gln Glu Glu Tyr Gly Gly
            1075                1080                1085

Ala Tyr Thr Ser Arg Asn Arg Gly Tyr Asn Glu Ala Pro Ser Val Pro
            1090                1095                1100

Ala Asp Tyr Ala Ser Val Tyr Glu Glu Lys Ser Tyr Thr Asp Gly Arg
1105                1110                1115                1120

Arg Glu Asn Pro Cys Glu Phe Asn Arg Gly Tyr Arg Asp Tyr Thr Pro
                1125                1130                1135

Leu Pro Val Gly Tyr Val Thr Lys Glu Leu Glu Tyr Phe Pro Glu Thr
```

```
                1140            1145            1150
Asp Lys Val   Trp Ile Glu  Ile Gly  Glu Thr Glu  Gly Thr  Phe Ile Val
        1155                    1160                1165

Asp Ser  Val Glu Leu  Leu Leu  Met Glu Glu
    1170                1175

<210> SEQ ID NO 8
<211> LENGTH: 3537
<212> TYPE: DNA
<213> ORGANISM: Bacillus thuringiensis

<400> SEQUENCE: 8
atggataaca atccgaacat caatgaatgc attccttata attgtttaag taaccctgaa      60
gtagaagtat taggtggaga agaatagaa  actggttaca ccccaatcga tatttccttg     120
tcgctaacgc aatttctttt gagtgaattt gttcccggtg ctggatttgt gttaggacta     180
gttgatataa tatggggaat ttttggtccc tctcaatggg acgcatttct tgtacaaatt     240
gaacagttaa ttaaccaaag aatagaagaa ttcgctagga accaagccat ttctagatta     300
gaaggactaa gcaatcttta tcaaatttac gcagaatctt ttagagagtg ggaagcagat     360
cctactaatc cagcattaag agaagagatg cgtattcaat tcaatgacat gaacagtgcc     420
cttacaaccg ctattcctct tttggcagtt caaaattatc aagttcctct tttatcagta     480
tatgttcaag ctgcaaattt acatttatca gttttgagag atgtttcagt gtttggacaa     540
aggtggggat ttgatgccgc gactatcaat agtcgttata atgatttaac taggcttatt     600
ggcaactata cagattatgc tgtacgctgg tacaatacgg gattagaacg tgtatgggga     660
ccggattcta gagattgggt aaggtataat caatttagaa gagaattaac actaactgta     720
ttagatatcg ttgctctgtt cccgaattat gatagtagaa gatatccaat tcgaacagtt     780
tcccaattaa caagagaaat ttatacaaac ccagtattag aaaattttga tggtagtttt     840
cgaggctcgg ctcagggcat agaaagaagt attaggagtc cacatttgat ggatatactt     900
aacagtataa ccatctatac ggatgctcat gggggttatt attattggtc agggcatcaa     960
ataatggctt ctcctgtcgg tttttcgggg ccagaattca cgtttccgct atatggaacc    1020
atgggaaatg cagctccaca caacgtatt  gttgctcaac taggtcaggg cgtgtataga    1080
acattatcgt ccactttata tagaagacct tttaatatag gataaataa tcaacaacta    1140
tctgttcttg acgggacaga atttgcttat ggaacctcct caaatttgcc atccgctgta    1200
tacagaaaaa gcggaacggt agattcgctg atgaaatac  cgccacagaa taacaacgtg    1260
ccacctaggc aaggatttag tcatcgatta agccatgttt caatgtttcg ttcaggcttt    1320
agtaatagta gtgtaagtat aataagagct cctatgttct cttggataca tcgtagtgct    1380
gaatttaata atataattgc atcggatagt attactcaaa tccctgcagt gaagggaaac    1440
tttcttttta atggttctgt aatttcagga ccaggattta ctggtgggga cttagttaga    1500
ttaaatagta gtggaaataa cattcagaat agagggtata ttgaagttcc aattcacttc    1560
ccatcgacat ctaccagata tcgagttcgt gtacggtatg cttctgtaac cccgattcac    1620
ctcaacgtta ttggggtaa  ttcatccatt ttttccaata cagtaccagc tacagctacg    1680
tcattagata atctacaatc aagtgatttt ggttattttg aaagtgccaa tgcttttaca    1740
tcttcattag gtaatatagt aggtgttaga aattttagtg ggactgcagg agtgataata    1800
gacagatttg aatttattcc agttactgca cactctgagg ctgaatataa tctgaaaga    1860
gcgcagaagg cggtgaatgc gctgtttacg tctacaaacc aactagggct aaaaacaaat    1920
```

| | |
|---|---:|
| gtaacggatt atcatattga tcaagtgtcc aatttagtta cgtatttatc ggatgaattt | 1980 |
| tgtctggatg aaaagcgaga attgtccgag aaagtcaaac atgcgaagcg actcagtgat | 2040 |
| gaacgcaatt tactccaaga ttcaaatttc aaagacatta ataggcaacc agaacgtggg | 2100 |
| tggggcggaa gtacagggat taccatccaa ggaggggatg acgtatttaa agaaaattac | 2160 |
| gtcacactat caggtacctt tgatgagtgc tatccaacat atttgtatca aaaaatcgat | 2220 |
| gaatcaaaat taaaagcctt tacccgttat caattaagag ggtatatcga agatagtcaa | 2280 |
| gacttagaaa tctatttaat tcgctacaat gcaaaacatg aaacagtaaa tgtgccaggt | 2340 |
| acgggttcct tatggccgct ttcagcccaa agtccaatcg aaagtgtgg agagccgaat | 2400 |
| cgatgcgcgc cacaccttga atggaatcct gacttagatt gttcgtgtag ggatggagaa | 2460 |
| aagtgtgccc atcattcgca tcatttctcc ttagacattg atgtaggatg tacagactta | 2520 |
| aatgaggacc taggtgtatg ggtgatcttt aagattaaga cgcaagatgg gcacgcaaga | 2580 |
| ctagggaatc tagagtttct cgaagagaaa ccattagtag gagaagcgct agctcgtgtg | 2640 |
| aaaagagcgg agaaaaaatg gagagacaaa cgtgaaaaat tggaatggga aacaaatatc | 2700 |
| gtttataaag aggcaaaaga atctgtagat gctttatttg taaactctca atatgatcaa | 2760 |
| ttacaagcgg atacgaatat tgccatgatt catgcggcag ataaacgtgt tcatagcatt | 2820 |
| cgagaagctt atctgcctga gctgtctgtg attccgggtg tcaatgcggc tattttttgaa | 2880 |
| gaattagaag ggcgtatttt cactgcattc tccctatatg atgcgagaaa tgtcattaaa | 2940 |
| aatggtgatt ttaataatgg cttatcctgc tggaacgtga agggcatgt agatgtagaa | 3000 |
| gaacaaaaca accaacgttc ggtccttgtt gttccggaat gggaagcaga agtgtcacaa | 3060 |
| gaagttcgtg tctgtccggg tcgtggctat atccttcgtg tcacagcgta caaggaggga | 3120 |
| tatgagaag gttgcgtaac cattcatgag atcgagaaca atacagacga actgaagttt | 3180 |
| agcaactgcg tagaagagga aatctatcca aataacacgg taacgtgtaa tgattatact | 3240 |
| gtaaatcaag aagaatacgg aggtgcgtac acttctcgta atcgaggata taacgaagct | 3300 |
| ccttccgtac cagctgatta tgcgtcagtc tatgaagaaa aatcgtatac agatggacga | 3360 |
| agagagaatc cttgtgaatt taacagaggg tatagggatt acacgccact accagttggt | 3420 |
| tatgtgacaa aagaattaga atacttccca gaaaccgata aggtatggat tgagattgga | 3480 |
| gaaacggaag gaacatttat cgtggacagc gtggaattac tccttatgga ggaatag | 3537 |

<210> SEQ ID NO 9
<211> LENGTH: 3966
<212> TYPE: DNA
<213> ORGANISM: Artificial sequence
<220> FEATURE:
<223> OTHER INFORMATION: Synthetic

<400> SEQUENCE: 9

| | |
|---|---:|
| atggacaaca acccgaacat caacgagtgc atcccctaca attgcctgag caaccctgaa | 60 |
| gtcgaggtgc tgggagggga gcgcatcgag accgggtaca cgccaataga catctcccctc | 120 |
| agcctcaccc agttcctgtt gtcggagttc gtgccgggcg cggggttcgt gctcgggctc | 180 |
| gtggacatca tctctgggca cttcggcccc agccagtggg acgccttcct tgtccagatc | 240 |
| gagcagctca tcaaccagcg gatcgaggag ttcgctcgca accaggcgat ctccgggctc | 300 |
| gaaggcctgt caaacctcta ccaaatctac gccgagagct tccgcgagtg ggaggcggac | 360 |
| ccaacaaacc ccgccctgcg cgaggagatg cgcatccagt tcaacgacat gaactccgcc | 420 |
| ctcaccactg ccatcccgct cctcgctgtg cagaactacc aagtcccctt gctgtcggtc | 480 |

```
tacgtccagg cggccaacct ccacctctcc gtgctgcgcg acgtcagcgt cttcgggcag    540
cgctggggct tcgacgccgc gaccatcaac agccgctaca acgacctgac ccgcctgatc    600
ggcaactaca ccgactacgc cgtgcggtgg tacaacacgg actggagag gtctggggga    660 ccggactcgc gggactgggt gcgctacaac cagttccgcc gggagctgac gctgaccgtc    720
ctcgacatcg tggcgctgtt ccccaactac gacagtcggc ggtacccgat ccgcaccgtc    780
tcccagctca cgagggaaat ctacacgaac ccggtgctgg agaactttga cggctccttc    840
agggggagcg cccagggcat cgagcggtcc atccgctcgc ctcacctcat ggacattctc    900
aactcgatca ccatatacac ggacgcccac cggggttact actactggag cggccaccag    960
atcatggctt ccccagtcgg cttcagcggt cccgagttca ccttcccgct gtacggcacg   1020
atgggcaacg cggccccaca gcagcgcatc gtcgcgcagc tcggccaggg cgtgtaccgc   1080
accctgtcca gcacgctcta ccgccgcccg ttcaacatag ggatcaacaa ccagcaactg   1140
agcgtcctag acggcacgga gttcgcgtac ggcacttcct ccaacttgcc gtctgccgtg   1200
taccggaagt ccgggacggt ggactccctc gacgagattc cgccgcagaa caacaacgtg   1260
ccgcctaggc agggcttctc tcaccggctg tcccacgttt ccatgttccg ctcgggcttc   1320
tctaactcgt ccgtgtcgat catcagggcc cctatgttct cctggattca tcgcagcgcg   1380
gaggtcaaca acatcattgc tagcgacagc ataacccaga tcccggccgt gaagggcaac   1440
ttcctgttca acggctcggt gatctccggt ccaggcttca caggaggcga cctggtccgg   1500
ctcaattcaa gcggcaacaa tatccagaat cgcggctaca tcgaggtgcc catacacttc   1560
ccatcgacca gcacgcgcta ccgcgtgcgg gtccgctacg cctcggtgac cccgatccac   1620
ctcaacgtca actggggcaa tagctccatc ttctccaaca ccgtgcccgc cacggcgacc   1680
tccctggaca acctccagtc cagcgacttt ggctacttcg agagcgcgaa cgctttcacc   1740
agctccctgg ggaacatcgt cggagtgagg aatttctccg gcacggctgg cgtcattatc   1800
gaccggtttg agttcatacc cgtcacggcg actctcgagc ctgagcgcat cacgcagatc   1860
ccactggtga aggcgcacac gctccagtcc ggcaccaccg tcgtcagggg ccctggcttc   1920
acgggcggcg acatcctccg tcgcacgtcc ggcggcccat tcgcgtacac gatcgtgaac   1980
atcaacggcc agctgccgca gcgctacagg gcgagaatcc gctacgcaag caccacgaac   2040
ctcaggatct acgtcaccgt cgccggggag cggatcttcg ctggccagtt caataagaca   2100
atggacaccg gcgacccact gaccttccag agcttctcgt acgccacgat caacacggcc   2160
ttcaccttcc cgatgagcca gtccagcttc accgtcgggg cggacacgtt ctcctccggc   2220
aacgaggtct acatcgaccg gttcgagctg atcccagtga ccctcgaggc ggagtacaac   2280
ctggagcgcg cgcagaaggc ggtcaacgcc ctcttcacga gcacgaacca gctcggcctc   2340
aagaccaacg tcaccgacta ccacatcgac caggtttcca acctggtgac ctacctcagc   2400
gacgagttct gcctcgacga aaagcgcgag ctgtccgaga agtcaagca cgccaagcgc   2460 ctcagcgacg agcgtaatct cctgcaagac tctaacttca aggacatcaa ccgccagccg   2520
gagaggggct ggggtgggtc caccggcata accattcagg gaggcgacga cgtcttcaag   2580
gagaactacg tcacgctctc cggaaccttc gacgagtgct acccaaccta cctgtaccag   2640
aaaatcgacg agagcaagct caaggccttc acgcgctacc agctccgtgg ctacatcgag   2700
gacagtcagg acctcgaaat ctacctcatc cgctacaatg cgaagcacga gacggtcaat   2760
gtgccgggca ccgggagcct ctggccgctg tccgcgcagt ccccaatcgg aaagtgcggg   2820
gagccgaacc gctgcgcccc gcacctggaa tggaacccgg acctcgactg ctcctgccgc   2880
```

-continued

```
gacggcgaga agtgcgcgca tcatagccac cacttcagcc tggacatcga cgtcggatgt    2940
actgacctga acgaggacct gggcgtgtgg gtcatcttca agatcaagac ccaggacggg    3000
cacgcccgcc tgggcaacct ggagttcctg gaggagaagc ccctggtggg agaggccctg    3060
gccagggtga agcgggcgga gaagaagtgg cgcgacaaac gcgagaagct ggagtgggag    3120
accaacatcg tctacaagga ggccaaggag tccgtggacg ccttgttcgt gaactcgcag    3180
tacgaccagc tccaggccga cacgaacatc gcgatgatcc atgctgccga caagcgggtc    3240
cactcgatcc gcgaggcgta cctgccggag ctgtcggtga tacccggcgt caacgccgcg    3300
atattcgagg agcttgaggg acgcatcttc acggccttca gcctctacga cgccaggaac    3360
gtcatcaaga acggggactt caacaacggc ctgtcctgct ggaatgtgaa gggtcacgtg    3420
gacgtggagg agcagaacaa ccagcgctcg gtcctcgtcg ttcccgagtg ggaagcggaa    3480
gtatcgcagg aggtgcgggt ctgtccgggc cgtggctaca tcctcagggt caccgcctac    3540
aaggaaggct acgcgagggg ctgcgtgacg atccacgaga tcgagaacaa cacggacgag    3600
ctgaaattct cgaattgcgt ggaggaggaa atctaccccca caacacggt tacctgcaac    3660 gactacacgg tgaaccagga ggagtacggc ggcgcctaca cctcccgcaa caggggctac    3720
aacgaggccc cgagcgtccc ggcggattac gcctccgtgt acgaggagaa gtcctacacc    3780 gacgccgcc gcgagaatcc gtgcgagttc aaccgcggtt accgagacta caccccactg    3840
cccgtcggct acgtgaccaa ggagctggag tacttcccgg agaccgacaa ggtctggatc    3900
gagatcgggg agaccgaggg gacattcatc gtcgacagcg tggagctgct cctcatggag    3960
gagtga                                                              3966
```

<210> SEQ ID NO 10
<211> LENGTH: 5453
<212> TYPE: DNA
<213> ORGANISM: Artificial sequence
<220> FEATURE:
<223> OTHER INFORMATION: Synthetic

<400> SEQUENCE: 10

```
ggtccgattg agactttttca acaaagggta atatccggaa acctcctcgg attccattgc      60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa     180
gatggacccc cacccacgag gagcatcgtg gaaaagaag acgttccaac cacgtcttca     240
aagcaagtgg attgatgtga tggtccgatt gagactttttc aacaaagggt aatatccgga     300
aacctcctcg gattccattg cccagctatc tgtcacttta ttgtgaagat agtggaaaag     360
gaaggtggct cctacaaatg ccatcattgc gataaaggaa aggccatcgt tgaagatgcc     420
tctgccgaca gtggtcccaa agatggaccc ccacccacga ggagcatcgt ggaaaagaa     480 gacgttccaa ccacgtcttc aaagcaagtg gattgatgtg atatctccac tgacgtaagg     540
gatgacgcac aatcccacta tccttcgcaa gacccttcct ctatataagg aagttcattt     600
catttggaga ggacacgctg acaagctgac tctagcagat cctctagaac catcttccac     660
acactcaagc cacactattg agaacacac agggacaaca caccataaga tccaagggag     720
gcctccgccg ccgccggtaa ccaccccgcc cctctcctct ttcttttctcc gttttttttt     780 ccgtctcggt ctcgatcttt ggccttggta gtttgggtgg gcgagaggcg gcttcgtgcg     840
cgcccagatc ggtgcgcggg aggggcggga tctcgcggct ggggctctcg ccggcgtgga     900
tccggcccgg atctcgcggg gaatgggggct ctcggatgta gatctgcgat ccgccgttgt     960
```

```
tgggggagat gatgggggt ttaaaatttc cgccgtgcta aacaagatca ggaagagggg    1020
aaaagggcac tatggtttat attttatat atttctgctg cttcgtcagg cttagatgtg    1080
ctagatcttt ctttcttctt tttgtgggta gaatttgaat ccctcagcat tgttcatcgg    1140
tagtttttct tttcatgatt tgtgacaaat gcagcctcgt gcggagcttt tttgtaggta    1200
gaagtgatca agggcccggt accctcagca gtcgctgtgc gataccatgg acaacaaccc    1260
gaacatcaac gagtgcatcc cctacaattg cctgagcaac cctgaagtcg aggtgctggg    1320
aggggagcgc atcgagaccg gtacacgcc aatagacatc tccctcagcc tcacccagtt    1380
cctgttgtcg gagttcgtgc cgggcgcggg gttcgtgctc gggctcgtgg acatcatctg    1440 ggcatcttc ggcccagcc agtgggacgc cttccttgtc cagatcgagc agctcatcaa    1500
ccagcggatc gaggagttcg ctcgcaacca ggcgatctcc cggctcgaag cctgtcaaa    1560 cctctaccaa atctacgccg agagcttccg cgagtgggag gcggacccaa caaacccgc    1620 cctgcgcgag gagatgcgca tccagttcaa cgacatgaac tccgccctca ccactgccat    1680
cccgctcctc gctgtgcaga actaccaagt cccttgctg tcggtctacg tccaggcggc    1740
caacctccac ctctccgtgc tgcgcgacgt cagcgtcttc gggcagcgct ggggcttcga    1800
cgccgcgacc atcaacagcc gctacaacga cctgacccgc ctgatcggca actacaccga    1860
ctacgccgtg cggtggtaca acacgggact ggagagggtc tggggaccgg actcgcggga    1920
ctgggtgcgc tacaaccagt tccgccggga gctgacgctg accgtcctcg acatcgtggc    1980
gctgttcccc aactacgaca gtcggcggta cccgatccgc accgtctccc agctcacgag    2040
ggaaatctac acgaacccgg tgctggagaa ctttgacggc tccttcaggg ggagcgccca    2100
gggcatcgag cggtccatcc gctcgcctca cctcatggac attctcaact cgatcaccat    2160
atacacggac gcccaccggg gttactacta ctggagcggc caccagatca tggcttcccc    2220
agtcggcttc agcggtcccg agttcacctt cccgctgtac ggcacgatgg gcaacgcggc    2280
cccacagcag cgcatcgtcg cgcagctcgg ccagggcgtg taccgcaccc tgtccagcac    2340
gctctaccgc cgcccgttca acatagggat caacaaccag caactgagcg tcctagacgg    2400
cacggagttc gcgtacggca cttcctccaa cttgccgtct gccgtgtacc ggaagtccgg    2460
gacggtggac tccctcgacg agattccgcc gcagaacaac aacgtgccgc ctaggcaggg    2520
cttctctcac cggctgtccc acgtttccat gttccgctcg ggcttctcta actcgtccgt    2580
gtcgatcatc agggccccta tgttctcctg gattcatcgc agcgcggagg tcaacaacat    2640
cattgctagc gacagcataa cccagatccc ggccgtgaag gcaacttcc tgttcaacgg    2700 ctcggtgatc tccggtccag gcttcacagg aggcgacctg gtccggctca attcaagcgg    2760
caacaatatc cagaatcgcg gctacatcga ggtgcccata cacttcccat cgaccagcac    2820
gcgctaccgc gtgcgggtcc gctacgcctc ggtgaccccg atccacctca cgtcaactg    2880 gggcaatagc tccatcttct ccaacaccgt gcccgccacg gcgacctccc tggacaacct    2940
ccagtccagc gactttggct acttcgagag cgcgaacgct ttcaccagct ccctggggaa    3000
catcgtcgga gtgaggaatt tctccggcac ggctggcgtc attatcgacc ggtttgagtt    3060
catacccgtc acggcgactc tcgagcctga gcgcatcacg cagatcccac tggtgaaggc    3120
gcacacgctc cagtccggca ccaccgtcgt caggggccct ggcttcacgg cggcgacat    3180 cctccgtcgc acgtccggcg gcccattcgc gtacacgatc gtgaacatca acggccagct    3240
gccgcagcgc tacaggcga gaatccgcta cgcaagcacc acgaacctca ggatctacgt    3300
caccgtcgcc ggggagcgga tcttcgctgg ccagttcaat aagacaatgg acaccggcga    3360
```

-continued

| | |
|---|---|
| cccactgacc ttccagagct tctcgtacgc cacgatcaac acggccttca ccttcccgat | 3420 |
| gagccagtcc agcttcaccg tcggggcgga cacgttctcc tccggcaacg aggtctacat | 3480 |
| cgaccggttc gagctgatcc cagtgaccct cgaggcggag tacaacctgg agcgcgcgca | 3540 |
| gaaggcggtc aacgccctct tcacgagcac gaaccagctc ggcctcaaga ccaacgtcac | 3600 |
| cgactaccac atcgaccagg tttccaacct ggtgacctac ctcagcgacg agttctgcct | 3660 |
| cgacgaaaag cgcgagctgt ccgagaaagt caagcacgcc aagcgcctca gcgacgagcg | 3720 |
| taatctcctg caagactcta acttcaagga catcaaccgc cagccggaga ggggctgggg | 3780 |
| tgggtccacc ggcataacca ttcagggagg cgacgacgtc ttcaaggaga actacgtcac | 3840 |
| gctctccgga accttcgacg agtgctaccc aacctacctg taccagaaaa tcgacgagag | 3900 |
| caagctcaag gccttcacgc gctaccagct ccgtggctac atcgaggaca gtcaggacct | 3960 |
| cgaaatctac ctcatccgct acaatgcgaa gcacgagacg gtcaatgtgc cgggcaccgg | 4020 |
| gagcctctgg ccgctgtccg cgcagtcccc aatcggaaag tgcggggagc cgaaccgctg | 4080 |
| cgccccgcac ctggaatgga acccggacct cgactgctcc tgccgcgacg gcgagaagtg | 4140 |
| cgcgcatcat agccaccact tcagcctgga catcgacgtc ggatgtactg acctgaacga | 4200 |
| ggacctgggc gtgtgggtca tcttcaagat caagacccag gacgggcacg cccgcctggg | 4260 |
| caacctggag ttcctggagg agaagccccc ggtgggagag gccctggcca gggtgaagcg | 4320 |
| ggcggagaag aagtggcgcg acaaacgcga gaagctggag tgggagacca catcgtcta | 4380 |
| caaggaggcc aaggagtccg tggacgcctt gttcgtgaac tcgcagtacg accagctcca | 4440 |
| ggccgacacg aacatcgcga tgatccatgc tgccgacaag cgggtccact cgatccgcga | 4500 |
| ggcgtacctg ccggagctgt cggtgatacc cggcgtcaac gccgcgatat tcgaggagct | 4560 |
| tgagggacgc atcttcacgg ccttcagcct ctacgacgcc aggaacgtca tcaagaacgg | 4620 |
| ggacttcaac aacggcctgt cctgctggaa tgtgaagggt cacgtggacg tggaggagca | 4680 |
| gaacaaccag cgctcggtcc tcgtcgttcc cgagtgggaa gcggaagtat cgcaggaggt | 4740 |
| gcgggtctgt ccgggccgtg gctacatcct caggtcacc gcctacaagg aaggctacgg | 4800 |
| cgagggctgc gtgacgatcc acgagatcga gaacaacacg gacgagctga aattctcgaa | 4860 |
| ttgcgtggag gaggaaatct accccaacaa cacggttacc tgcaacgact acacggtgaa | 4920 |
| ccaggaggag tacggcggcg cctacacctc ccgcaacagg ggctacaacg aggccccgag | 4980 |
| cgtcccggcg gattacgcct ccgtgtacga ggagaagtcc tacaccgacg gccgccgcga | 5040 |
| gaatccgtgc gagttcaacc gcggttaccg agactacacc ccactgcccg tcggctacgt | 5100 |
| gaccaaggag ctggagtact tcccggagac cgacaaggtc tggatcgaga tcggggagac | 5160 |
| cgagggggaca ttcatcgtcg acagcgtgga gctgctcctc atggaggagt gaatcgccag | 5220 |
| cggtactcgc tgaggttaat taactgcatg cgtttggacg tatgctcatt caggttggag | 5280 |
| ccaatttggt tgatgtgtgt gcgagttctt gcgagtctga tgagacatct ctgtattgtg | 5340 |
| tttctttccc cagtgttttc tgtacttgtg taatcggcta atcgccaaca gattcggcga | 5400 |
| tgaataaatg agaaataaat tgttctgatt ttgagtgcaa aaaaaagga att | 5453 |

<210> SEQ ID NO 11
<211> LENGTH: 1397
<212> TYPE: PRT
<213> ORGANISM: Artificial sequence
<220> FEATURE:
<223> OTHER INFORMATION: Synthetic

<400> SEQUENCE: 11

```
Met Ala Gln Val Ser Arg Ile Cys Asn Gly Val Gln Asn Pro Ser Leu
 1               5                  10                  15
Ile Ser Asn Leu Ser Lys Ser Ser Gln Arg Lys Ser Pro Leu Ser Val
             20                  25                  30
Ser Leu Lys Thr Gln Gln His Pro Arg Ala Tyr Pro Ile Ser Ser Ser
         35                  40                  45
Trp Gly Leu Lys Lys Ser Gly Met Thr Leu Ile Gly Ser Glu Leu Arg
     50                  55                  60
Pro Leu Lys Val Met Ser Ser Val Ser Thr Ala Cys Met Asp Asn Asn
 65                  70                  75                  80
Pro Asn Ile Asn Glu Cys Ile Pro Tyr Asn Cys Leu Ser Asn Pro Glu
                 85                  90                  95
Val Glu Val Leu Gly Gly Glu Arg Ile Glu Thr Gly Tyr Thr Pro Ile
                100                 105                 110
Asp Ile Ser Leu Ser Leu Thr Gln Phe Leu Leu Ser Glu Phe Val Pro
            115                 120                 125
Gly Ala Gly Phe Val Leu Gly Leu Val Asp Ile Ile Trp Gly Ile Phe
        130                 135                 140
Gly Pro Ser Gln Trp Asp Ala Phe Leu Val Gln Ile Glu Gln Leu Ile
145                 150                 155                 160
Asn Gln Arg Ile Glu Glu Phe Ala Arg Asn Gln Ala Ile Ser Arg Leu
                165                 170                 175
Glu Gly Leu Ser Asn Leu Tyr Gln Ile Tyr Ala Glu Ser Phe Arg Glu
            180                 185                 190
Trp Glu Ala Asp Pro Thr Asn Pro Ala Leu Arg Glu Glu Met Arg Ile
        195                 200                 205
Gln Phe Asn Asp Met Asn Ser Ala Leu Thr Thr Ala Ile Pro Leu Leu
210                 215                 220
Ala Val Gln Asn Tyr Gln Val Pro Leu Leu Ser Val Tyr Val Gln Ala
225                 230                 235                 240
Ala Asn Leu His Leu Ser Val Leu Arg Asp Val Ser Val Phe Gly Gln
                245                 250                 255
Arg Trp Gly Phe Asp Ala Ala Thr Ile Asn Ser Arg Tyr Asn Asp Leu
            260                 265                 270
Thr Arg Leu Ile Gly Asn Tyr Thr Asp Tyr Ala Val Arg Trp Tyr Asn
        275                 280                 285
Thr Gly Leu Glu Arg Val Trp Gly Pro Asp Ser Arg Asp Trp Val Arg
    290                 295                 300
Tyr Asn Gln Phe Arg Arg Glu Leu Thr Leu Thr Val Leu Asp Ile Val
305                 310                 315                 320
Ala Leu Phe Pro Asn Tyr Asp Ser Arg Arg Tyr Pro Ile Arg Thr Val
                325                 330                 335
Ser Gln Leu Thr Arg Glu Ile Tyr Thr Asn Pro Val Leu Glu Asn Phe
            340                 345                 350
Asp Gly Ser Phe Arg Gly Ser Ala Gln Gly Ile Glu Arg Ser Ile Arg
        355                 360                 365
Ser Pro His Leu Met Asp Ile Leu Asn Ser Ile Thr Ile Tyr Thr Asp
    370                 375                 380
Ala His Arg Gly Tyr Tyr Tyr Trp Ser Gly His Gln Ile Met Ala Ser
385                 390                 395                 400
Pro Val Gly Phe Ser Gly Pro Glu Phe Thr Phe Pro Leu Tyr Gly Thr
                405                 410                 415
Met Gly Asn Ala Ala Pro Gln Gln Arg Ile Val Ala Gln Leu Gly Gln
            420                 425                 430
```

```
Gly Val Tyr Arg Thr Leu Ser Ser Thr Leu Tyr Arg Arg Pro Phe Asn
            435                 440                 445

Ile Gly Ile Asn Asn Gln Gln Leu Ser Val Leu Asp Gly Thr Glu Phe
450                 455                 460

Ala Tyr Gly Thr Ser Ser Asn Leu Pro Ser Ala Val Tyr Arg Lys Ser
465                 470                 475                 480

Gly Thr Val Asp Ser Leu Asp Glu Ile Pro Pro Gln Asn Asn Asn Val
                485                 490                 495

Pro Pro Arg Gln Gly Phe Ser His Arg Leu Ser His Val Ser Met Phe
            500                 505                 510

Arg Ser Gly Phe Ser Asn Ser Val Ser Ile Ile Arg Ala Pro Met
            515                 520                 525

Phe Ser Trp Ile His Arg Ser Ala Glu Val Asn Asn Ile Ile Ala Ser
            530                 535                 540

Asp Ser Ile Thr Gln Ile Pro Ala Val Lys Gly Asn Phe Leu Phe Asn
545                 550                 555                 560

Gly Ser Val Ile Ser Gly Pro Gly Phe Thr Gly Gly Asp Leu Val Arg
                565                 570                 575

Leu Asn Ser Ser Gly Asn Asn Ile Gln Asn Arg Gly Tyr Ile Glu Val
                580                 585                 590

Pro Ile His Phe Pro Ser Thr Ser Thr Arg Tyr Arg Val Arg Val Arg
            595                 600                 605

Tyr Ala Ser Val Thr Pro Ile His Leu Asn Val Asn Trp Gly Asn Ser
            610                 615                 620

Ser Ile Phe Ser Asn Thr Val Pro Ala Thr Ala Thr Ser Leu Asp Asn
625                 630                 635                 640

Leu Gln Ser Ser Asp Phe Gly Tyr Phe Glu Ser Ala Asn Ala Phe Thr
                645                 650                 655

Ser Ser Leu Gly Asn Ile Val Gly Val Arg Asn Phe Ser Gly Thr Ala
            660                 665                 670

Gly Val Ile Ile Asp Arg Phe Glu Phe Ile Pro Val Thr Ala Thr Leu
            675                 680                 685

Glu Pro Glu Arg Ile Thr Gln Ile Pro Leu Val Lys Ala His Thr Leu
690                 695                 700

Gln Ser Gly Thr Thr Val Val Arg Gly Pro Gly Phe Thr Gly Gly Asp
705                 710                 715                 720

Ile Leu Arg Arg Thr Ser Gly Gly Pro Phe Ala Tyr Thr Ile Val Asn
                725                 730                 735

Ile Asn Gly Gln Leu Pro Gln Arg Tyr Arg Ala Arg Ile Arg Tyr Ala
            740                 745                 750

Ser Thr Thr Asn Leu Arg Ile Tyr Val Thr Val Ala Gly Glu Arg Ile
            755                 760                 765

Phe Ala Gly Gln Phe Asn Lys Thr Met Asp Thr Gly Asp Pro Leu Thr
770                 775                 780

Phe Gln Ser Phe Ser Tyr Ala Thr Ile Asn Thr Ala Phe Thr Phe Pro
785                 790                 795                 800

Met Ser Gln Ser Ser Phe Thr Val Gly Ala Asp Thr Phe Ser Ser Gly
                805                 810                 815

Asn Glu Val Tyr Ile Asp Arg Phe Glu Leu Ile Pro Val Thr Leu Glu
            820                 825                 830

Ala Glu Tyr Asn Leu Glu Arg Ala Gln Lys Ala Val Asn Ala Leu Phe
            835                 840                 845

Thr Ser Thr Asn Gln Leu Gly Leu Lys Thr Asn Val Thr Asp Tyr His
```

```
              850              855              860
Ile Asp Gln Val Ser Asn Leu Val Thr Tyr Leu Ser Asp Glu Phe Cys
865              870              875              880

Leu Asp Glu Lys Arg Glu Leu Ser Glu Lys Val Lys His Ala Lys Arg
              885              890              895

Leu Ser Asp Glu Arg Asn Leu Leu Gln Asp Ser Asn Phe Lys Asp Ile
              900              905              910

Asn Arg Gln Pro Glu Arg Gly Trp Gly Gly Ser Thr Gly Ile Thr Ile
              915              920              925

Gln Gly Gly Asp Asp Val Phe Lys Glu Asn Tyr Val Thr Leu Ser Gly
              930              935              940

Thr Phe Asp Glu Cys Tyr Pro Thr Tyr Leu Tyr Gln Lys Ile Asp Glu
945              950              955              960

Ser Lys Leu Lys Ala Phe Thr Arg Tyr Gln Leu Arg Gly Tyr Ile Glu
              965              970              975

Asp Ser Gln Asp Leu Glu Ile Tyr Leu Ile Arg Tyr Asn Ala Lys His
              980              985              990

Glu Thr Val Asn Val Pro Gly Thr Gly Ser Leu Trp Pro Leu Ser Ala
              995              1000             1005

Gln Ser Pro Ile Gly Lys Cys Gly Glu Pro Asn Arg Cys Ala Pro His
              1010             1015             1020

Leu Glu Trp Asn Pro Asp Leu Asp Cys Ser Cys Arg Asp Gly Glu Lys
1025             1030             1035             1040

Cys Ala His His Ser His His Phe Ser Leu Asp Ile Asp Val Gly Cys
              1045             1050             1055

Thr Asp Leu Asn Glu Asp Leu Gly Val Trp Val Ile Phe Lys Ile Lys
              1060             1065             1070

Thr Gln Asp Gly His Ala Arg Leu Gly Asn Leu Glu Phe Leu Glu Glu
              1075             1080             1085

Lys Pro Leu Val Gly Glu Ala Leu Ala Arg Val Lys Arg Ala Glu Lys
              1090             1095             1100

Lys Trp Arg Asp Lys Arg Glu Lys Leu Glu Trp Glu Thr Asn Ile Val
1105             1110             1115             1120

Tyr Lys Glu Ala Lys Glu Ser Val Asp Ala Leu Phe Val Asn Ser Gln
              1125             1130             1135

Tyr Asp Gln Leu Gln Ala Asp Thr Asn Ile Ala Met Ile His Ala Ala
              1140             1145             1150

Asp Lys Arg Val His Ser Ile Arg Glu Ala Tyr Leu Pro Glu Leu Ser
              1155             1160             1165

Val Ile Pro Gly Val Asn Ala Ala Ile Phe Glu Glu Leu Glu Gly Arg
              1170             1175             1180

Ile Phe Thr Ala Phe Ser Leu Tyr Asp Ala Arg Asn Val Ile Lys Asn
1185             1190             1195             1200

Gly Asp Phe Asn Asn Gly Leu Ser Cys Trp Asn Val Lys Gly His Val
              1205             1210             1215

Asp Val Glu Glu Gln Asn Asn Gln Arg Ser Val Leu Val Val Pro Glu
              1220             1225             1230

Trp Glu Ala Glu Val Ser Gln Glu Val Arg Val Cys Pro Gly Arg Gly
              1235             1240             1245

Tyr Ile Leu Arg Val Thr Ala Tyr Lys Glu Gly Tyr Gly Glu Gly Cys
              1250             1255             1260

Val Thr Ile His Glu Ile Glu Asn Asn Thr Asp Glu Leu Lys Phe Ser
1265             1270             1275             1280
```

```
Asn Cys Val Glu Glu  Glu Ile Tyr Pro Asn  Asn Thr Val Thr Cys  Asn
            1285                 1290                  1295

Asp Tyr Thr Val  Asn Gln Glu Glu Tyr  Gly Gly Ala Tyr Thr  Ser Arg
        1300                 1305                  1310

Asn Arg Gly  Tyr Asn Glu Ala Pro  Ser Val Pro Ala Asp  Tyr Ala Ser
    1315                 1320                  1325

Val Tyr Glu Glu Lys  Ser Tyr Thr Asp Gly  Arg Arg Glu Asn Pro  Cys
            1330                 1335                  1340

Glu Phe Asn Arg Gly  Tyr Arg Asp Tyr Thr  Pro Leu Pro Val Gly  Tyr
1345                 1350                  1355                 1360

Val Thr Lys Glu Leu  Glu Tyr Phe Pro Glu  Thr Asp Lys Val Trp  Ile
            1365                 1370                  1375

Glu Ile Gly Glu  Thr Glu Gly Thr Phe  Ile Val Asp Ser Val  Glu Leu
        1380                 1385                  1390

Leu Leu Met  Glu Glu
    1395

<210> SEQ ID NO 12
<211> LENGTH: 4194
<212> TYPE: DNA
<213> ORGANISM: Artificial sequence
<220> FEATURE:
<223> OTHER INFORMATION: Synthetic

<400> SEQUENCE: 12
atggctcaag tgtcgcgcat ctgtaacgga gttcagaacc ctagcctgat ctctaacttg      60
agcaagtcta gccagcgtaa gtcaccattg agcgtgagct tgaagactca acagcaccct     120
agagcctacc caataagctc tagttgggga ctcaagaagt ccggtatgac tctgattgga     180
tctgagttac gtcctctgaa agtgatgagt tccgttagta ccgcttgcat ggacaacaac     240
ccgaacatca acgagtgcat ccctacaat tgcctgagca accctgaagt cgaggtgctg      300 ggagggagc gcatcgagac cgggtacacg ccaatagaca tctccctcag cctcacccag      360
ttcctgttgt cggagttcgt gccgggcgcg gggttcgtgc tcgggctcgt ggacatcatc     420
tggggcatct tcggccccag ccagtgggac gccttccttg tccagatcga gcagctcatc     480
aaccagcgga tcgaggagtt cgctcgcaac caggcgatct cccggctcga aggcctgtca     540
aacctctacc aaatctacgc cgagagcttc gcgagtgggg aggcggaccc aacaaacccc     600
gccctgcgcg aggagatgcg catccagttc aacgacatga actccgccct caccactgcc     660
atcccgctcc tcgctgtgca gaactaccaa gtccccttgc tgtcggtcta cgtccaggcg     720
gccaacctcc acctctccgt gctgcgcgac gtcagcgtct cgggcagcg ctggggcttc      780 gacgccgcga ccatcaacag ccgctacaac gacctgaccc cgctgatcgg caactacacc     840
gactacgccg tgcggtggta caacacggga ctggagaggg tctggggacc ggactcgcgg     900
gactgggtgc gctacaacca gttccgccgg gagctgacgc tgaccgtcct cgacatcgtg     960
gcgctgttcc ccaactacga cagtcggcgg tacccgatcc gcaccgtctc ccagctcacg    1020
agggaaatct acacgaaccc ggtgctggag aactttgacg gctcccttcag ggggagcgcc   1080 cagggcatcg agcggtccat ccgctcgcct cacctcatgg acattctcaa ctcgatcacc    1140
atatacacgg acgcccaccg gggttactac tactggagcg ccaccagat catggcttcc    1200 ccagtcggct tcagcggtcc cgagttcacc ttcccgctgt acggcacgat gggcaacgcg    1260
gccccacagc agcgcatcgt cgcgcagctc ggccagggcg tgtaccgcac cctgtccagc    1320
acgctctacc gccgcccgtt caacataggg atcaacaacc agcaactgag cgtcctagac    1380
```

-continued

| | |
|---|---|
| ggcacggagt tcgcgtacgg cacttcctcc aacttgccgt ctgccgtgta ccggaagtcc | 1440 |
| gggacggtgg actccctcga cgagattccg ccgcagaaca caacgtgcc gcctaggcag | 1500 |
| ggcttctctc accggctgtc ccacgttcc atgttccgct cgggcttctc taactcgtcc | 1560 |
| gtgtcgatca tcagggcccc tatgttctcc tggattcatc gcagcgcgga ggtcaacaac | 1620 |
| atcattgcta gcgacagcat aacccagatc ccggccgtga agggcaactt cctgttcaac | 1680 |
| ggctcggtga tctccggtcc aggcttcaca ggaggcgacc tggtccggct caattcaagc | 1740 |
| ggcaacaata tccagaatcg cggctacatc gaggtgccca tacacttccc atcgaccagc | 1800 |
| acgcgctacc gcgtgcgggt ccgctacgcc tcggtgaccc cgatccacct caacgtcaac | 1860 |
| tggggcaata gctccatctt ctccaacacc gtgcccgcca cggcgacctc cctggacaac | 1920 |
| ctccagtcca gcgactttgg ctacttcgag agcgcgaacg ctttcaccag ctccctgggg | 1980 |
| aacatcgtcg gagtgaggaa tttctccggc acggctggcg tcattatcga ccggtttgag | 2040 |
| ttcatacccg tcacggcgac tctcgagcct gagcgcatca cgcagatccc actggtgaag | 2100 |
| gcgcacacgc tccagtccgg caccaccgtc gtcaggggcc ctggcttcac gggcggcgac | 2160 |
| atcctccgtc gcacgtccgg cggcccattc gcgtacacga tcgtgaacat caacggccag | 2220 |
| ctgccgcagc gctacagggc gagaatccgc tacgcaagca ccacgaacct caggatctac | 2280 |
| gtcaccgtcg ccggggagcg gatcttcgct ggccagttca ataagacaat ggacaccggc | 2340 |
| gacccactga ccttccagag cttctcgtac gccacgatca acacggcctt caccttcccg | 2400 |
| atgagccagt ccagcttcac cgtcggggcg gacacgttct cctccggcaa cgaggtctac | 2460 |
| atcgaccggt tcgagctgat cccagtgacc ctcgaggcgg agtacaacct ggagcgcgcg | 2520 |
| cagaaggcgg tcaacgccct cttcacgagc acgaaccagc tcggcctcaa gaccaacgtc | 2580 |
| accgactacc acatcgacca ggtttccaac ctggtgacct acctcagcga cgagttctgc | 2640 |
| ctcgacgaaa agcgcgagct gtccgagaaa gtcaagcacg ccaagcgcct cagcgacgag | 2700 |
| cgtaatctcc tgcaagactc taacttcaag gacatcaacc gccagccgga gaggggctgg | 2760 |
| ggtgggtcca ccggcataac cattcaggga ggcgacgacg tcttcaagga gaactacgtc | 2820 |
| acgctctccg gaaccttcga cgagtgctac ccaacctacc tgtaccagaa aatcgacgag | 2880 |
| agcaagctca aggccttcac gcgctaccag ctccgtggct acatcgagga cagtcaggac | 2940 |
| ctcgaaatct acctcatccg ctacaatgcg aagcacgaga cggtcaatgt gccgggcacc | 3000 |
| gggagcctct ggccgctgtc cgcgcagtcc ccaatcggaa agtgcgggga gccgaaccgc | 3060 |
| tgcgccccgc acctggaatg gaaccccgac ctcgactgct cctgccgcga cggcgagaag | 3120 |
| tgcgcgcatc atagccacca cttcagcctg gacatcgacg tcggatgtac tgacctgaac | 3180 |
| gaggacctgg gcgtgtgggt catcttcaag atcaagaccc aggacgggca cgcccgcctg | 3240 |
| ggcaacctgg agttcctgga ggagaagccc ctggtgggag aggccctggc cagggtgaag | 3300 |
| cgggcggaga agaagtggcg cgacaaacgc gagaagctgg agtgggagac caacatcgtc | 3360 |
| tacaaggagg ccaaggagtc cgtggacgcc ttgttcgtga actcgcagta cgaccagctc | 3420 |
| caggccgaca cgaacatcgc gatgatccat gctgccgaca gcgggtcca ctcgatccgc | 3480 |
| gaggcgtacc tgccggagct gtcggtgata cccggcgtca acgccgcgat attcgaggag | 3540 |
| cttgagggac gcatcttcac ggccttcagc ctctacgacg ccaggaacgt catcaagaac | 3600 |
| ggggacttca caacggcct gtcctgctgg aatgtgaagg gtcacgtgga cgtggaggag | 3660 |
| cagaacaacc agcgctcggt cctcgtcgtt cccgagtggg aagcggaagt atcgcaggag | 3720 |
| gtgcgggtct gtccgggccg tggctacatc ctcagggtca ccgcctacaa ggaaggctac | 3780 |

-continued

| | |
|---|---|
| ggcgagggct gcgtgacgat ccacgagatc gagaacaaca cggacgagct gaaattctcg | 3840 |
| aattgcgtgg aggaggaaat ctaccccaac aacacggtta cctgcaacga ctacacggtg | 3900 |
| aaccaggagg agtacggcgg cgcctacacc tcccgcaaca ggggctacaa cgaggccccg | 3960 |
| agcgtcccgg cggattacgc ctccgtgtac gaggagaagt cctacaccga cggccgccgc | 4020 |
| gagaatccgt gcgagttcaa ccgcggttac cgagactaca ccccactgcc cgtcggctac | 4080 |
| gtgaccaagg agctggagta cttcccggag accgacaagg tctggatcga gatcggggag | 4140 |
| accgagggga cattcatcgt cgacagcgtg gagctgctcc tcatggagga gtga | 4194 |

<210> SEQ ID NO 13
<211> LENGTH: 5681
<212> TYPE: DNA
<213> ORGANISM: Artificial sequence
<220> FEATURE:
<223> OTHER INFORMATION: Synthetic

<400> SEQUENCE: 13

| | |
|---|---|
| ggtccgattg agacttttca acaaagggta atatccggaa acctcctcgg attccattgc | 60 |
| ccagctatct gtcactttat tgtgaagata gtggaaaagg aaggtggctc ctacaaatgc | 120 |
| catcattgcg ataaaggaaa ggccatcgtt gaagatgcct ctgccgacag tggtcccaaa | 180 |
| gatggacccc cacccacgag gagcatcgtg aaaaagaag acgttccaac cacgtcttca | 240 |
| aagcaagtgg attgatgtga tggtccgatt gagacttttc aacaaagggt aatatccgga | 300 |
| aacctcctcg gattccattg cccagctatc tgtcacttta ttgtgaagat agtgaaaaag | 360 |
| gaaggtggct cctacaaatg ccatcattgc gataaaggaa aggccatcgt tgaagatgcc | 420 |
| tctgccgaca gtggtcccaa agatggaccc ccacccacga ggagcatcgt ggaaaaagaa | 480 |
| gacgttccaa ccacgtcttc aaagcaagtg gattgatgtg atatctccac tgacgtaagg | 540 |
| gatgacgcac aatcccacta ccttcgcaa gacccttcct ctatataagg aagttcattt | 600 |
| catttggaga ggacacgctg acaagctgac tctagcagat cctctagaac catcttccac | 660 |
| acactcaagc cacactattg gagaacacac agggacaaca caccataaga tccaagggag | 720 |
| gcctccgccg ccgccggtaa ccaccccgcc cctctcctct ttctttctcc gtttttttt | 780 |
| ccgtctcggt ctcgatcttt ggccttggta gtttgggtgg gcgagaggcg gcttcgtgcg | 840 |
| cgcccagatc ggtgcgcggg aggggcggga tctcgcggct ggggctctcg ccggcgtgga | 900 |
| tccggcccgg atctcgcggg gaatgggct ctcggatgta gatctgcgat ccgccgttgt | 960 |
| tgggggagat gatgggggt ttaaaatttc cgccgtgcta acaagatca ggaagagggg | 1020 |
| aaaagggcac tatggtttat attttatat atttctgctg cttcgtcagg cttagatgtg | 1080 |
| ctagatcttt ctttcttctt tttgtgggta gaatttgaat ccctcagcat tgttcatcgg | 1140 |
| tagttttct tttcatgatt tgtgacaaat gcagcctcgt gcggagcttt tttgtaggta | 1200 |
| gaagtgatca agggcccggt accctcagca gtcgctgtgc gataccatgg ctcaagtgtc | 1260 |
| gcgcatctgt aacggagttc agaaccctag cctgatctct aacttgagca agtctagcca | 1320 |
| gcgtaagtca ccattgagcg tgagcttgaa gactcaacag caccctagag cctacccaat | 1380 |
| aagctctagt tggggactca agaagtccgg tatgactctg attggatctg agttacgtcc | 1440 |
| tctgaaagtg atgagttccg ttagtaccgc ttgcatggaa acaacccga acatcaacga | 1500 |
| gtgcatcccc tacaattgcc tgagcaaccc tgaagtcgag gtgctgggag gggagcgcat | 1560 |
| cgagaccggg tacacgccaa tagacatctc cctcagcctc acccagttcc tgttgtcgga | 1620 |
| gttcgtgccg ggcgcggggt tcgtgctcgg gctcgtggac atcatctggg gcatcttcgg | 1680 |

| | |
|---|---|
| ccccagccag tgggacgcct tccttgtcca gatcgagcag ctcatcaacc agcggatcga | 1740 |
| ggagttcgct cgcaaccagg cgatctcccg gctcgaaggc ctgtcaaacc tctaccaaat | 1800 |
| ctacgccgag agcttccgcg agtgggaggc ggacccaaca aaccccgccc tgcgcgagga | 1860 |
| gatgcgcatc cagttcaacg acatgaactc cgccctcacc actgccatcc cgctcctcgc | 1920 |
| tgtgcagaac taccaagtcc ccttgctgtc ggtctacgtc caggcggcca acctccacct | 1980 |
| ctccgtgctg cgcgacgtca gcgtcttcgg gcagcgctgg ggcttcgacg ccgcgaccat | 2040 |
| caacagccgc tacaacgacc tgacccgcct gatcggcaac tacaccgact acgccgtgcg | 2100 |
| gtggtacaac acgggactgg agagggtctg ggaccggac tcgcgggact gggtgcgcta | 2160 |
| caaccagttc cgccgggagc tgacgctgac cgtcctcgac atcgtggcgc tgttccccaa | 2220 |
| ctacgacagt cggcggtacc cgatccgcac cgtctcccag ctcacgaggg aaatctacac | 2280 |
| gaacccggtg ctggagaact tgacggctc cttcaggggg agcgcccagg gcatcgagcg | 2340 |
| gtccatccgc tcgcctcacc tcatggacat tctcaactcg atcaccatat acacggacgc | 2400 |
| ccaccggggt tactactact ggagcggcca ccagatcatg gcttccccag tcggcttcag | 2460 |
| cggtcccgag ttcaccttcc cgctgtacgg cacgatgggc aacgcggccc acagcagcg | 2520 |
| catcgtcgcg cagctcggcc agggcgtgta ccgcaccctg tccagcacgc tctaccgccg | 2580 |
| cccgttcaac atagggatca acaaccagca actgagcgtc ctagacggca cggagttcgc | 2640 |
| gtacggcact tcctccaact tgccgtctgc cgtgtaccgg aagtccggga cggtggactc | 2700 |
| cctcgacgag attccgccgc agaacaacaa cgtgccgcct aggcagggct tctctcaccg | 2760 |
| gctgtcccac gtttccatgt tccgctcggg cttctctaac tcgtccgtgt cgatcatcag | 2820 |
| ggcccctatg ttctcctgga ttcatcgcag cgcggaggtc aacaacatca ttgctagcga | 2880 |
| cagcataacc cagatcccgg ccgtgaaggg caacttcctg ttcaacggct cggtgatctc | 2940 |
| cggtccaggc ttcacaggag gcgacctggt ccggctcaat tcaagcggca acaatatcca | 3000 |
| gaatcgcggc tacatcgagg tgcccataca cttcccatcg accagcacgc gctaccgcgt | 3060 |
| gcgggtccgc tacgcctcgg tgaccccgat ccacctcaac gtcaactggg gcaatagctc | 3120 |
| catcttctcc aacaccgtgc ccgccacggc gacctccctg acaacctcc agtccagcga | 3180 |
| ctttggctac ttcgagagcg cgaacgcttt caccagctcc ctggggaaca tcgtcggagt | 3240 |
| gaggaatttc tccggcacgg ctggcgtcat tatcgaccgg tttgagttca tacccgtcac | 3300 |
| ggcgactctc gagcctgagc gcatcacgca gatcccactg gtgaaggcgc acacgctcca | 3360 |
| gtccggcacc accgtcgtca ggggccctgg cttcacgggc ggcgacatcc tccgtcgcac | 3420 |
| gtccggcggc ccattcgcgt acacgatcgt gaacatcaac ggccagctgc cgcagcgcta | 3480 |
| cagggcgaga atccgctacg caagcaccac gaacctcagg atctacgtca ccgtcgccgg | 3540 |
| ggagcggatc ttcgctggcc agttcaataa gacaatggac accggcgacc cactgacctt | 3600 |
| ccagagcttc tcgtacgcca cgatcaacac ggccttcacc ttcccgatga gccagtccag | 3660 |
| cttcaccgtc ggggcggaca cgttctcctc cggcaacgag gtctacatcg accggttcga | 3720 |
| gctgatccca gtgaccctcg aggcggagta caacctggag cgcgcgcaga aggcggtcaa | 3780 |
| cgccctcttc acgagcacga accagctcgg cctcaagacc aacgtcaccg actaccacat | 3840 |
| cgaccaggtt tccaacctgg tgacctacct cagcgacgag ttctgcctcg acgaaaagcg | 3900 |
| cgagctgtcc gagaaagtca agcacgccaa gcgcctcagc gacgagcgta atctcctgca | 3960 |
| agactctaac ttcaaggaca tcaaccgcca gccggagagg ggctgggtg ggtccaccgg | 4020 |
| cataaccatt cagggaggcg acgacgtctt caaggagaac tacgtcacgc tctccggaac | 4080 |

-continued

```
cttcgacgag tgctacccaa cctacctgta ccagaaaatc gacgagagca agctcaaggc    4140
cttcacgcgc taccagctcc gtggctacat cgaggacagt caggacctcg aaatctacct    4200
catccgctac aatgcgaagc acgagacggt caatgtgccg ggcaccggga gcctctggcc    4260
gctgtccgcg cagtcccaa tcggaaagtg cggggagccg aaccgctgcg ccccgcacct    4320
ggaatggaac ccggacctcg actgctcctg ccgcgacggc gagaagtgcg cgcatcatag    4380
ccaccacttc agcctggaca tcgacgtcgg atgtactgac ctgaacgagg acctgggcgt    4440
gtgggtcatc ttcaagatca agacccagga cgggcacgcc cgcctgggca acctggagtt    4500
cctggaggag aagcccctgg tgggagaggc cctggccagg gtgaagcggg cggagaagaa    4560
gtggcgcgac aaacgcgaga agctggagtg ggagaccaac atcgtctaca aggaggccaa    4620
ggagtccgtg gacgccttgt tcgtgaactc gcagtacgac cagctccagg ccgacacgaa    4680
catcgcgatg atccatgctg ccgacaagcg ggtccactcg atccgcgagg cgtacctgcc    4740
ggagctgtcg gtgatacccg gcgtcaacgc cgcgatattc gaggagcttg agggacgcat    4800
cttcacggcc ttcagcctct acgacgccag gaacgtcatc aagaacgggg acttcaacaa    4860
cggcctgtcc tgctggaatg tgaagggtca cgtggacgtg gaggagcaga acaaccagcg    4920
ctcggtcctc gtcgttcccg agtgggaagc ggaagtatcg caggaggtgc gggtctgtcc    4980
gggccgtggc tacatcctca gggtcaccgc ctacaaggaa ggctacgcg agggctgcgt    5040 gacgatccac gagatcgaga acaacacgga cgagctgaaa ttctcgaatt gcgtggagga    5100
ggaaatctac cccaacaaca cggttacctg caacgactac acggtgaacc aggaggagta    5160
cggcggcgcc tacacctccc gcaacagggg ctacaacgag gccccgagcg tcccggcgga    5220
ttacgcctcc gtgtacgagg agaagtccta caccgacggc cgccgcgaga atccgtgcga    5280
gttcaaccgc ggttaccgag actacacccc actgcccgtc ggctacgtga ccaaggagct    5340
ggagtacttc ccggagaccg acaaggtctg gatcgagatc ggggagaccg aggggacatt    5400
catcgtcgac agcgtggagc tgctcctcat ggaggagtga atcgccagcg gtactcgctg    5460
aggttaatta actgcatgcg tttggacgta tgctcattca ggttggagcc aatttggttg    5520
atgtgtgtgc gagttcttgc gagtctgatg agacatctct gtattgtgtt tctttcccca    5580
gtgttttctg tacttgtgta atcggctaat cgccaacaga ttcggcgatg aataaatgag    5640
aaataaattg ttctgatttt gagtgcaaaa aaaaaggaat t                        5681
```